(12) United States Patent
Gill et al.

(10) Patent No.: US 12,303,377 B2
(45) Date of Patent: May 20, 2025

(54) DYNAMIC FIXATION IMPLANT AND METHOD OF USE

(71) Applicant: Paragon 28, Inc., Englewood, CO (US)

(72) Inventors: Sean Patrick Gill, Denver, CO (US); Kaitlin Karas, Denver, CO (US)

(73) Assignee: Paragon 28, Inc., Englewood, CO (US)

( * ) Notice: Subject to any disclaimer, the term of this patent is extended or adjusted under 35 U.S.C. 154(b) by 527 days.

(21) Appl. No.: 17/693,665

(22) Filed: Mar. 14, 2022

(65) Prior Publication Data

US 2022/0192817 A1 Jun. 23, 2022

Related U.S. Application Data

(63) Continuation of application No. PCT/US2020/050438, filed on Sep. 11, 2020.
(Continued)

(51) Int. Cl.
*A61F 2/08* (2006.01)

(52) U.S. Cl.
CPC ..... *A61F 2/0811* (2013.01); *A61F 2002/0835* (2013.01); *A61F 2250/0007* (2013.01)

(58) Field of Classification Search
CPC ............ A61F 2/0811; A61F 2002/0835; A61F 2250/0007; A61B 17/16; A61B 17/1682;
(Continued)

(56) References Cited

U.S. PATENT DOCUMENTS 3,268,965 A 8/1966 Arthur
3,343,443 A 9/1967 Moore
(Continued)

FOREIGN PATENT DOCUMENTS

CN 102670291 9/2012
CN 102920498 2/2013
(Continued)

OTHER PUBLICATIONS

Porucznik, "Screw vs. tightrope fixation for syndesmotic fractures," AAOS NOW, http://www.aaos.org/news/aaosnow/may08/clinical4.asp, 3 pages, May 2008.
(Continued)

*Primary Examiner* — Melanie R Tyson
*Assistant Examiner* — Paris Marie Blass
(74) *Attorney, Agent, or Firm* — Heslin Rothenberg Farley & Mesiti P.C.

(57) ABSTRACT

Implants and related methods for achieving dynamic fixation are disclosed. The implant comprises a head portion at a proximal end of the implant comprising external threads and a first axial through hole, and an anchor portion extending from the head portion at a distal end of the implant comprising external threads and a second axial through hole in communication with the first axial through hole. The implant further comprises a flexible constraint member extending within the first and second axial through holes comprising a first end portion coupled to the head portion and a second end portion coupled to the anchor portion. At least one of the head portion and the anchor portions forms a breakaway portion with aligned internal and external circumferential grooves configured to concentrate stress thereat such that the breakaway portion fractures via forces acting on the implant to separate the head and anchor portions.

28 Claims, 39 Drawing Sheets

Related U.S. Application Data

(60) Provisional application No. 62/899,559, filed on Sep. 12, 2019.

(58) Field of Classification Search
CPC . A61B 17/72; A61B 17/8625; A61B 17/8685; A61B 17/84; A61B 17/68
See application file for complete search history.

(56) References Cited

U.S. PATENT DOCUMENTS

| | | | |
|---|---|---|---|
| 3,953,896 A | 5/1976 | Treace | |
| 4,463,753 A | 8/1984 | Gustilo | |
| 4,955,910 A | 9/1990 | Bolesky | |
| 5,004,474 A | 4/1991 | Fronk | |
| 5,061,137 A * | 10/1991 | Gourd | F16B 21/088 411/908 |
| 5,152,790 A | 10/1992 | Rosenberg | |
| 5,486,197 A | 1/1996 | Le | |
| 5,507,812 A | 4/1996 | Moore | |
| 5,702,397 A | 12/1997 | Goble | |
| 5,743,912 A | 4/1998 | Lahille | |
| 5,968,045 A | 10/1999 | Frazier | |
| 5,971,987 A | 10/1999 | Huxel | |
| 6,187,008 B1 | 2/2001 | Hamman | |
| 6,461,373 B2 | 10/2002 | Wyman | |
| 6,620,195 B2 | 9/2003 | Goble | |
| 6,652,592 B1 | 11/2003 | Grooms | |
| 6,921,402 B2 | 7/2005 | Contiliano | |
| 7,235,078 B2 | 6/2007 | West, Jr. | |
| 7,235,091 B2 | 6/2007 | Thornes | |
| 7,608,098 B1 | 10/2009 | Stone | |
| 7,625,395 B2 * | 12/2009 | Muckter | A61B 17/866 606/300 |
| 7,727,278 B2 | 6/2010 | Olsen | |
| 7,955,388 B2 | 6/2011 | Jensen | |
| 8,128,696 B2 | 3/2012 | Mayr | |
| 8,202,295 B2 | 6/2012 | Kaplan | |
| 8,439,976 B2 | 5/2013 | Albertorio | |
| 8,529,611 B2 | 9/2013 | Champagne | |
| 8,597,337 B2 | 12/2013 | Champagne | |
| 8,668,419 B2 | 3/2014 | Hardt | |
| 8,696,716 B2 | 4/2014 | Kartalian | |
| 8,696,719 B2 | 4/2014 | Lofthouse | |
| 8,753,380 B2 | 6/2014 | Cheng | |
| 8,858,605 B1 | 10/2014 | Glatzer | |
| 8,864,804 B2 | 10/2014 | Champagne | |
| 9,089,371 B1 | 7/2015 | Faulhaber | |
| 9,138,219 B2 * | 9/2015 | Horrell | A61B 17/0401 |
| 9,345,522 B2 | 5/2016 | Songer | |
| 9,358,055 B2 | 6/2016 | Cheng | |
| 9,687,256 B2 | 6/2017 | Granberry | |
| 9,877,760 B2 | 1/2018 | Ehler | |
| 9,907,576 B2 | 3/2018 | Mahajan | |
| 10,070,896 B2 | 9/2018 | Biedermann | |
| 10,314,631 B2 | 6/2019 | Gonzalez Blohm | |
| 10,610,276 B2 | 4/2020 | Lutz | |
| 2002/0133156 A1 | 9/2002 | Cole | |
| 2002/0143333 A1 | 10/2002 | von Hoffmann | |
| 2004/0172032 A1 | 9/2004 | Jackson | |
| 2005/0059972 A1 | 3/2005 | Biscup | |
| 2007/0162124 A1 | 7/2007 | Whittaker | |
| 2007/0218750 A1 | 9/2007 | Corrao | |
| 2007/0282342 A1 | 12/2007 | Niederberger | |
| 2008/0182227 A1 | 7/2008 | Wolf | |
| 2008/0300638 A1 | 12/2008 | Beardsley | |
| 2009/0198287 A1 | 8/2009 | Chiu | |
| 2009/0210016 A1 * | 8/2009 | Champagne | A61B 17/863 606/104 |
| 2009/0306777 A1 | 12/2009 | Widmer | |
| 2011/0040335 A1 | 2/2011 | Stihl | |
| 2011/0184471 A1 | 7/2011 | Foley | |
| 2011/0276099 A1 | 11/2011 | Champagne | |
| 2011/0282387 A1 | 11/2011 | Suh | |
| 2012/0029579 A1 | 2/2012 | Bottlang | |
| 2012/0041395 A1 | 2/2012 | Sweeney | |
| 2012/0123474 A1 | 5/2012 | Zajac | |
| 2012/0150237 A1 * | 6/2012 | Combrowski | A61B 17/8891 606/301 |
| 2012/0172936 A1 * | 7/2012 | Horrell | A61B 17/0401 606/104 |
| 2012/0209332 A1 | 8/2012 | Janowski | |
| 2012/0271416 A1 | 10/2012 | Mackay | |
| 2012/0303038 A1 | 11/2012 | Durante | |
| 2013/0030480 A1 | 1/2013 | Donate | |
| 2013/0090691 A1 | 4/2013 | Zhang et al. | |
| 2013/0131733 A1 | 5/2013 | Chien | |
| 2013/0131737 A1 | 5/2013 | Cheng | |
| 2013/0178901 A1 | 7/2013 | Arai | |
| 2013/0184708 A1 | 7/2013 | Robinson et al. | |
| 2013/0317503 A1 | 11/2013 | Songer | |
| 2013/0338722 A1 * | 12/2013 | Yalizis | A61B 17/68 606/312 |
| 2014/0025166 A1 | 1/2014 | Bonutti | |
| 2014/0121711 A1 | 5/2014 | Worcel | |
| 2014/0214095 A1 | 7/2014 | Rosenwasser et al. | |
| 2014/0228866 A1 | 8/2014 | Fallin et al. | |
| 2014/0236237 A1 | 8/2014 | Manhajan | |
| 2014/0243977 A1 | 8/2014 | Tepic | |
| 2014/0276894 A1 | 9/2014 | Ramsay et al. | |
| 2014/0277444 A1 | 9/2014 | Clifford et al. | |
| 2015/0051601 A1 | 2/2015 | Larsen et al. | |
| 2015/0073475 A1 | 3/2015 | Schaller | |
| 2015/0081019 A1 | 3/2015 | Whittaker | |
| 2015/0272646 A1 | 10/2015 | Russell | |
| 2015/0289866 A1 | 10/2015 | Bowen | |
| 2015/0342656 A1 | 12/2015 | Bertollo | |
| 2016/0030035 A1 | 2/2016 | Zajac et al. | |
| 2016/0045636 A1 | 2/2016 | Rizk et al. | |
| 2016/0287301 A1 | 10/2016 | Mehl et al. | |
| 2016/0287302 A1 | 10/2016 | Horrell et al. | |
| 2016/0354183 A1 | 12/2016 | Montero | |
| 2016/0367303 A1 | 12/2016 | Mahajan | |
| 2016/0367341 A1 | 12/2016 | Pérez Yanini | |
| 2017/0079698 A1 | 3/2017 | Fallin et al. | |
| 2017/0079699 A1 | 3/2017 | Fallin et al. | |
| 2017/0112552 A1 | 4/2017 | Sinnott et al. | |
| 2017/0258572 A1 * | 9/2017 | Gordon | A61B 17/1782 |
| 2018/0078299 A1 | 3/2018 | Rossney et al. | |
| 2018/0092681 A1 | 4/2018 | Lutz | |
| 2018/0221072 A1 | 8/2018 | P | |
| 2018/0344374 A1 | 12/2018 | Summitt | |
| 2019/0083232 A1 * | 3/2019 | Dacosta | A61B 17/92 |
| 2019/0090926 A1 | 3/2019 | Lutz et al. | |
| 2019/0125420 A1 | 5/2019 | Diaz et al. | |
| 2019/0336190 A1 | 11/2019 | Allard et al. | |
| 2019/0336270 A1 | 11/2019 | Dacosta et al. | |
| 2020/0323565 A1 | 10/2020 | Childs | |

FOREIGN PATENT DOCUMENTS

| | | | |
|---|---|---|---|
| DE | 19943594 | 4/2001 | |
| DE | 10015734 | 9/2001 | |
| DE | 102010055433 | 6/2012 | |
| GR | 20090100297 | 12/2010 | |
| JP | 2003010199 | 1/2003 | |
| WO | 2006124987 | 11/2006 | |
| WO | 2010121234 | 10/2010 | |
| WO | 2013015754 | 1/2013 | |
| WO | 2016133938 | 8/2016 | |
| WO | WO-2016133938 A1 * | 8/2016 | A61B 17/84 |
| WO | 2019071273 | 4/2019 | |

OTHER PUBLICATIONS

Xu et al., "Flexible fixation of syndesmotic diastasis using the assembled bolt-tightrope system," Scandinavian Journal of Trauma, Resuscitation and Emergency Medicine, vol. 21(71), 9 pages, 2013.
"Interventional procedure overview of suture fixation of acute disruption of the distal tibiofibular syndesmosis," National Institute for Health and Care Excellence, www.nice.org.uk, 43 pages, Jul. 2014.

(56) References Cited

OTHER PUBLICATIONS

International Search Report and Written Opinion of the International Searching Authority for PCT/US2020/050438, Dec. 10, 2020, 9 pages.
International Preliminary Report on Patentability for International Application No. PCT/US2020/050438 dated Mar. 15, 2022, 6 pages, International Bureau of WIPO.
Extended European Search Report for European Application No. 20863144.0, Aug. 25, 2023, 5 pages.

* cited by examiner

DYNAMIC FIXATION IMPLANT AND METHOD OF USE

CROSS REFERENCE TO RELATED APPLICATION

This application is a by-pass continuation of PCT International Application No. PCT/US2020/050438, filed Sep. 11, 2020, and entitled "Dynamic Fixation Implant and Method of Use," which claims priority benefit under 35 U.S.C. § 119(e) of U.S. Provisional Patent Application No. 62/899,559, filed Sep. 12, 2019, and entitled "Dynamic Fixation Implant and Method of Use," which are incorporated herein by reference in their entireties.

TECHNICAL FIELD

The present disclosure relates generally to general, podiatric, and orthopaedic surgery related to fixation of ligaments. More specifically, but not exclusively, the present disclosure relates to devices, systems, and methods for achieving dynamic ligament fixation.

BACKGROUND

Syndesmotic injuries are a result of trauma (not specific to sports injuries) and can occur as a purely ligamentous injury or in combination with an ankle fracture. These ligaments become disrupted, separated, or injured where semi-constrained approximation and fixation is needed to aide in healing without the need for a second surgery such as removal of a rigid fixation screw. The current standard of care for syndesmotic injuries involves either rigid fixation with a screw, or a tether-based constraint across the entire width of the ankle.

The more rigid screw-based fixation is simple to implant and stabilizes the joint, but fails to allow any motion at all, as would normally exist physiologically. This limits the patient's range of motion, and unpredictable screw failure locations can result in damage to existing bone and patient pain.

Tethered constraints, currently commercially available, do allow for motion of the joint, but by spanning the entire width of the ankle, fail to mimic the intact ligament structures of the syndesmosis in terms of attachment location and distance between the tibia and fibula. However, tethered constraints result in a necessary decrease in structural strength due to the surgical technique for the implant and involve drilling a hole through both the tibia and fibula which remains unfilled by structural material (e.g. a metal screw).

Thus, new and improved devices, systems, and methods for achieving ligament fixation are needed to overcome the above-noted drawbacks of the currently available solutions for addressing syndesmotic injuries.

SUMMARY

The present disclosure is directed toward implants and methods for use in fixation. The implants and methods may be configured to achieve dynamic ligament fixation.

In one aspect, the present disclosure provides an implant comprising a head portion at a proximal end of the implant comprising external threads and a first axial through hole, an anchor portion extending from the head portion at a distal end of the implant comprising external threads and a second axial through hole in communication with the first axial through hole, and a flexible constraint member extending within the first and second axial through holes comprising a first end portion coupled to the head portion and a second end portion coupled to the anchor portion. At least one of the head portion and the anchor portions forms a breakaway portion configured to concentrate stress thereat such that the implant fractures at the breakaway portion via forces acting on the implant to separate the head and anchor portions. The breakaway portion comprises an external circumferential groove and an internal circumferential groove axially aligned with the external groove, the internal circumferential groove formed at least in part by an internal end surface portion of the head portion and an internal end surface portion of the anchor portion.

In some embodiments, the internal end surface portion of the head portion comprises and an internal arcuate end surface portion of the head portion, and the internal end surface portion of the anchor portion comprises and an internal arcuate end surface portion of the anchor portion. In some embodiments, the internal end surface portion of the head portion comprises and an internal beveled end surface portion of the head portion, and the internal end surface portion of the anchor portion comprises and an internal beveled end surface portion of the anchor portion.

In some embodiments, a proximal end portion of the anchor portion comprises a coupling cavity and a distal end portion of the head portion comprises a coupling projection corresponding to the coupling cavity, the coupling projection being received within the coupling cavity. In some embodiments, a bottom portion of the coupling cavity defines the internal end surface portion of the anchor portion, and a tip portion of the coupling projection defines the internal end surface portion of the head portion. In some embodiments, the coupling cavity and the coupling projection are welded together.

In some embodiments, the head portion and the anchor portion are welded together. In some embodiments, the head portion and the anchor portion are laser welded together.

In some embodiments, the head portion and the anchor portion are welded together at a weld zone that is positioned axially adjacent to the external and internal external grooves. In some embodiments, the weld zone comprises the coupling projection and the coupling cavity welded together.

In some embodiments, the flexible constraint member comprises an elastic member. In some embodiments, the flexible constraint member comprises a suture loop.

In some embodiments, the implant further comprises a head post member retained within an enlarged portion of the first axial through hole, and the head post member is coupled to a first end portion of the flexible constraint member. In some embodiments, a resilient member is positioned within the enlarged portion of the first axial through hole axially between a proximal end of the enlarged portion and the head post member.

In some embodiments, the implant further comprises an anchor post member positioned within the second axial through hole and fixedly coupled to the anchor portion, and the anchor post member is coupled to a second end portion of the flexible constraint member. In some embodiments, a proximal end portion of the anchor post member comprises at least one hook. In some embodiments, the anchor post member comprises an external groove, and a coupling portion of the anchor member is deformed into the external groove.

In some embodiments, the head portion comprises a shaft portion with a first end and a second end, a head extending from the first end of the shaft portion, and a first breakaway coupling portion extending from the second end of the shaft portion. In some embodiments, a portion of the shaft portion of the head portion comprises external threads. In some embodiments, the head comprises a non-circular drive opening at an axial free end thereof, the non-circular drive opening forming a portion of the first axial through hole. In some embodiments, the first breakaway coupling portion comprises a coupling projection with an inner surface that defines the internal end surface portion of the head portion, the inner surface of the coupling projection forming a portion of the first axial through hole. In some embodiments, the first breakaway coupling portion further comprises a stop surface extending radially from an outer surface of the coupling projection and positioned axially between the internal end surface portion thereof and the head. In some embodiments, the anchor portion comprises a second breakaway coupling at a first end thereof comprising a coupling cavity with an inner bottom surface that defines the internal end surface portion of the anchor portion, the inner surface of the coupling projection forming a portion of the first axial through hole. In some embodiments, the coupling projection is mated within the coupling cavity. In some embodiments, the coupling projection and the coupling cavity are welded together. In some embodiments, an end surface of the second breakaway coupling abuts the stop surface of the first breakaway coupling.

In some embodiments, the anchor member further comprises a shaft portion with a first end and a second end, and a crimp portion extending from the second end, the second breakaway coupling extends from the first end of the shaft portion. In some embodiments, a portion of the shaft portion of the anchor member comprises external threads. In some embodiments, a proximal portion of the shaft portion comprises a plurality of outer planar surfaces circumferentially arranged about the proximal coupling portion that form a proximal external drive feature. In some embodiments, the crimp portion comprises a plurality of outer planar surfaces circumferentially arranged about the proximal coupling portion that form a distal external drive feature In some embodiments, the first axial through hole of the head portion comprises a first enlarged portion positioned proximate to the head and a second narrow portion positioned proximate to the breakaway portion, and the implant further comprises a head post member positioned within the first enlarged portion of the first axial through hole and coupled to the first end portion of the flexible constraint member. In some embodiments, the implant further comprises at least one resilient member positioned within the first enlarged portion of the first axial through hole axially between the second narrow portion thereof and the head post member. In some embodiments, the second narrow portion, the at least one resilient member and the head post member are configured such that the at least one resilient member and the head post member are prevented form axially translating through the second narrow portion. In some embodiments, the at least one resilient member comprises at least one tube formed of thermoplastic urethane, polycarbonate urethane or a combination thereof.

In some embodiments, the implant further comprises a tip post member positioned within the second axial through hole and coupled to the second end portion of the flexible constraint member. In some embodiments, the tip post member comprises a hook slot extending from an end of the tip post member positioned proximate to a distal free end of the implant. In some embodiments, the tip post member comprises a recess in an outer surface thereof, the recess configured to accept a deformed portion of the anchor portion therein to axially fix the tip post within the second axial through hole.

In some embodiments, the flexible constraint member comprises a suture. In some embodiments, the flexible constraint member comprises a loop.

In some embodiments, the head portion, the breakaway portion and the anchor member are integral. In some embodiments, the implant is integral. In some embodiments, a cannulated opening extends through an entire axial length of the implant.

In another aspect, the present disclosure provides a method of inserting an implant comprising obtaining an implant as disclosed herein, engaging the implant with an insertion instrument, and inserting the implant into a patient such that the head portion is positioned in a first bone, the anchor portion is positioned in a second bone, and the breakaway portion is positioned within a joint between the first and second bones.

In some embodiments, the first bone is a fibula and the second bone is a tibia. In some embodiments, the implant is inserted as a one piece construct. In some embodiments, the implant allows for motion between the first bone and the second bone after fracture of the breakaway portion at the external and internal circumferential grooves.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

DETAILED DESCRIPTION

Figure 1:
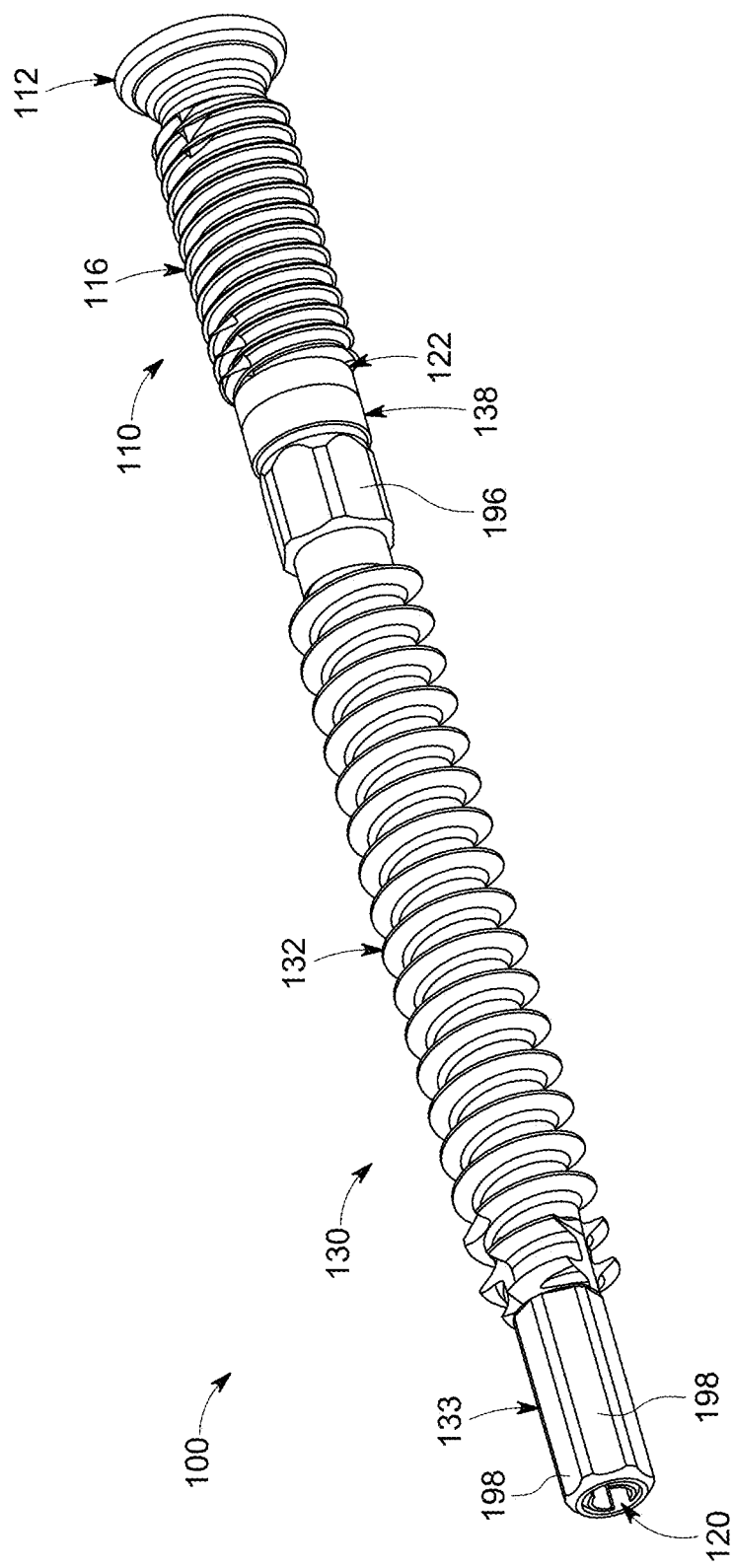
FIG. 1 illustrates a perspective side view of an exemplary dynamic fixation implant, in accordance with an aspect of the present disclosure.
Figure 2:
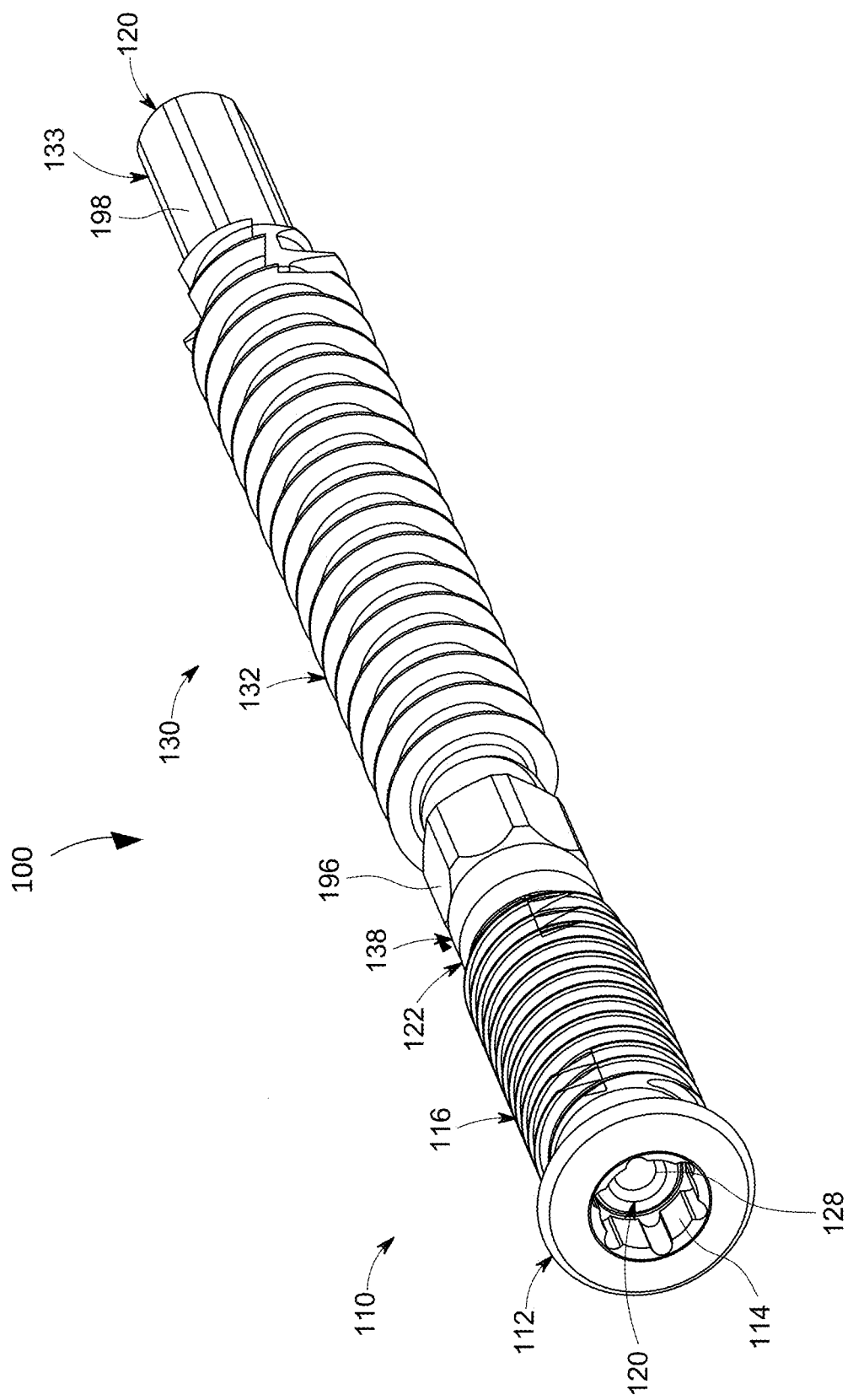
FIG. 2 illustrates another perspective side view of the implant of FIG. 1, in accordance with an aspect of the present disclosure.
Figure 3:
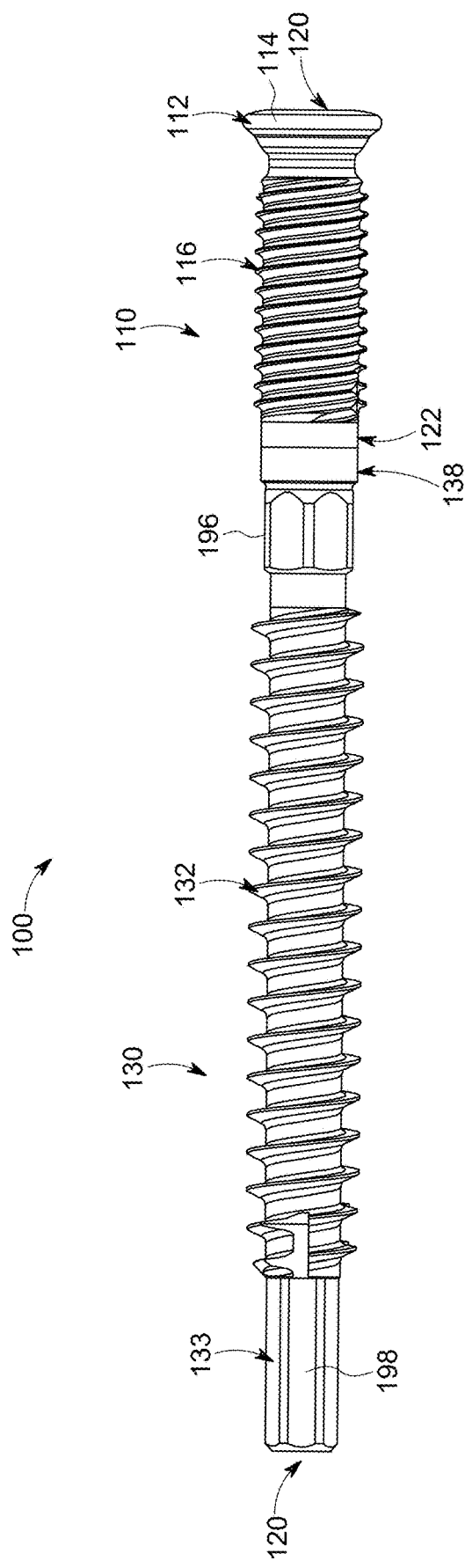
FIG. 3 illustrates a side view of the implant of FIG. 1, in accordance with an aspect of the present disclosure.
Figure 4:
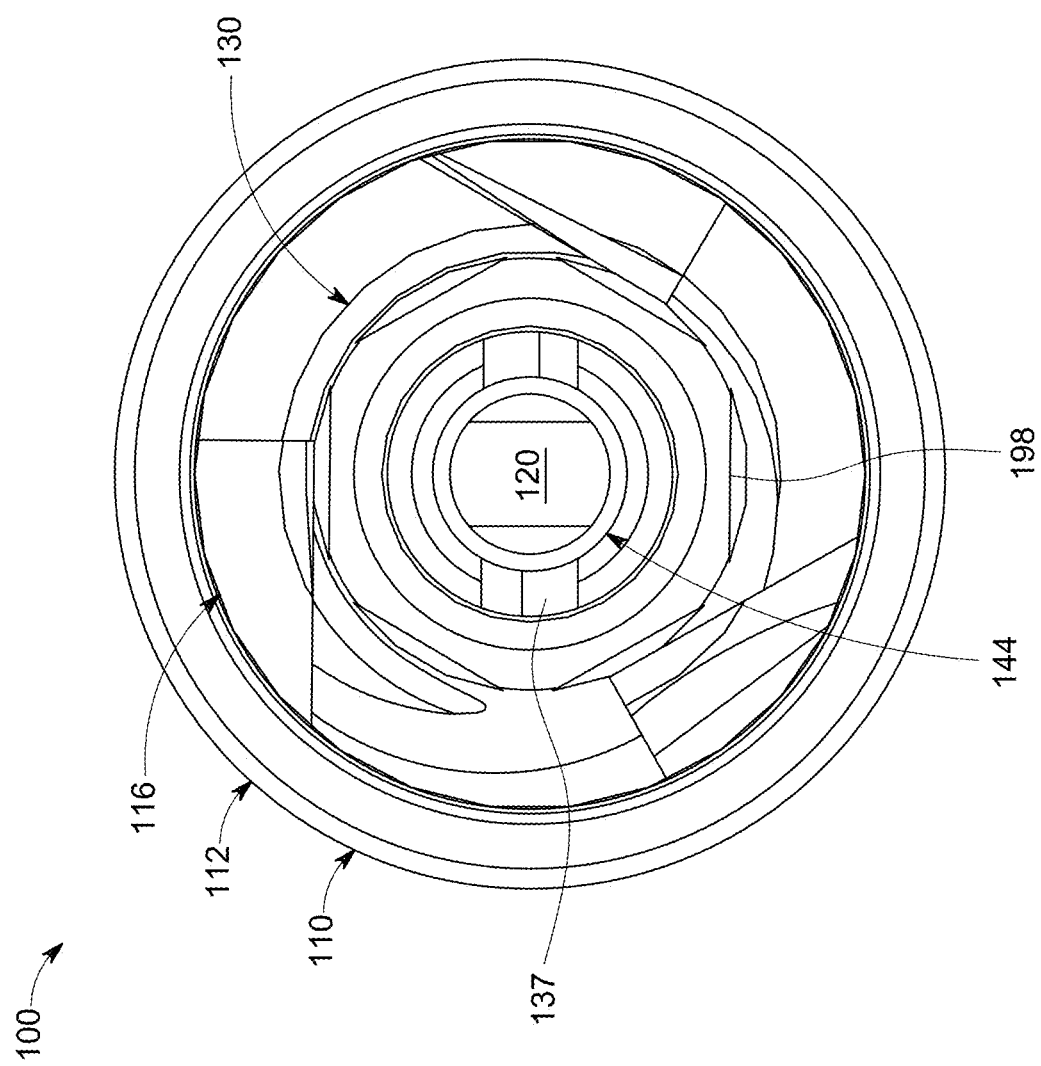
FIG. 4 illustrates an end view of the implant of FIG. 1, in accordance with an aspect of the present disclosure.
Figure 5:
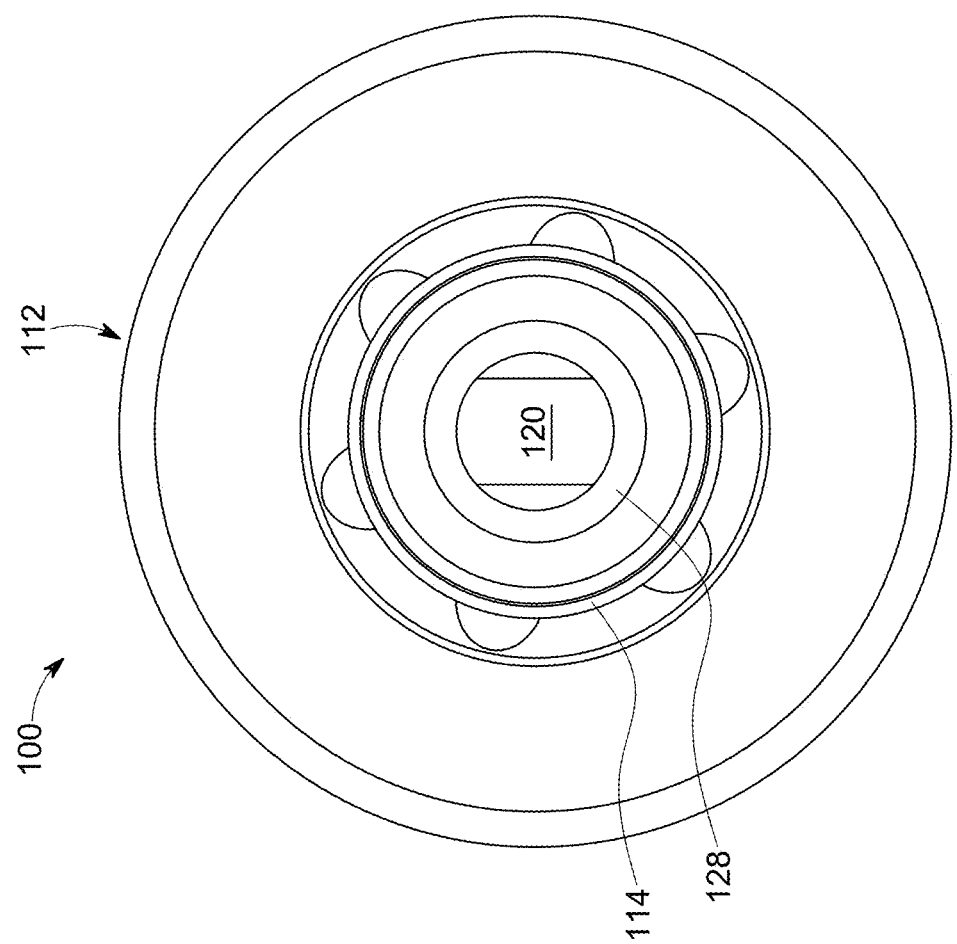
FIG. 5 illustrates another end view of the implant of FIG. 1, in accordance with an aspect of the present disclosure.

Generally stated, disclosed herein are devices and systems for achieving ligament fixation. Further, methods for using the devices and systems to achieve ligament fixation are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation and methods are described herein with reference to use with the bones of the ankle, the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the implants, devices, instrumentation and methods, and the aspects, components, features and the like thereof, described herein with respect to the right leg may be mirrored so that they likewise function with the left leg. Further, the implants, devices, instrumentation and methods, and the aspects, components, features and the like thereof, disclosed herein are described with respect to the leg for brevity purposes, but it should be understood that the implants, devices, instrumentation and methods may be used with other bones of the body having similar structures.

The implants, system and related methods disclosed herein are similar to that disclosed in International Patent Application No. PCT/US2018/057554 filed on Oct. 25, 2018, International Patent Application No. PCT/US2018/055028 filed on Oct. 9, 2018, and International Patent Application No. PCT/US2018/051349 filed on Sep. 17, 2018, which are hereby expressly incorporated herein in their entireties.

Referring to the drawings, wherein like reference numerals are used to indicate like or analogous components throughout the several views, and with particular reference to FIGS. 1-13 there is illustrated an implant 100. The implant 100 may be, for example, configured to heal syndesmotic ligaments post-operatively. The implant 100 is configured to selectively constrain motion between two or more bones in all directions to allow for one or more ligament extending therebetween to heal. After the ligament(s) (e.g., syndesmotic ligaments) heal, the implant 100 is configured to allow for physiologic motion between the bones or bone segments. With respect to syndesmotic ligaments, the implant 100 is also configured to re-create pressure in the lateral gutter.

The components and portions of the implant 100 may be made of, for example, titanium, stainless steel, polymers, polyester, UHMWPE, thermoplastic (e.g., thermoplastic urethane), bio-resorbable materials or any other biocompatible material.

As shown in FIGS. 1-13, the implant 100 provides for allow for screw-like implantation and temporary rigid fixation, then, after insertion, the implant 100 transitions and provides for semi-constrained motion. The temporary rigid fixation of the implant 100 gives the fixed joint a stabilized time period during healing, and then thereafter allows physiologic motion. The area of allowed semi-constrained motion provided by the implant 100 may be set in a space or gap between adjacent bones or bone segments (such as the fibula and tibia), where a subsequent risk of damage to native bone is lower. As shown in FIGS. 6-9, 11-13, 33 and 24, the implant 100 may include a flexible constraint and/or tension member or tether 150 that extends between proximal and distal portions of the implant 100, which may be elastic and configured to mimic the function, location and/or length of an interosseous ligament, for example. A surgical method for implanting the implant 100 may include forming (e.g., drilling) a hole or cavity through both the bones/bone segments (e.g., a tibia and a fibula), and then inserting the implant 100 sized to fill the bone holes or cavities to provide a strong fixed post-operative construct.

As shown in FIGS. 1-35, the implant 100 includes a head portion or member 110 (or fibula member), an anchor portion or member 130 (or tibia member), a coupling breakaway portion 160, a flexible constraint or tension member 150, a resilient member 150, a head post 128 and a tip post 144. The coupling breakaway portion 160 may be positioned between the head portion 110 and the anchor portion 130 as shown in FIGS. 1-13, and allow for the anchor portion 130 (and the head portion 110) to be secured into the bones as a single (integral) construct when the head portion 110 is torques or rotated about an axis of the implant 100. The tension member 150 may extend within/through a through hole or cannulation (i.e., cannulated opening) 120 of the implant 100 that extends at least partially thorough the head portion 110 and the anchor portion 130, as shown in FIGS. 6-9, 11-13 and 24 and described further below. The head portion 110, anchor portion 130, a flexible constraint or tension member 150, resilient member 150, head post 128 and/or tip post 144 may be made of, for example, titanium, stainless steel, polymer, or another biocompatible material as would be known by one of ordinary skill in the art.

In some embodiments, the implant 100 may have a total axial length of, for example, about 40 mm to about 70 mm. In some embodiments, the head portion 110 may have an axial length of, for example, between about 10 mm and 25 about mm, the anchor portion 130 may have a length of, for example, between approximately 15 mm and 65 mm. In one embodiment, the axial length of the head portion 110 may remain constant, while the axial length of the anchor portion 130 may be variable to correspond to varying sizes of a patient's bones. In this way, a system or kit according to the present disclosure may include a plurality of implants 100 of differing total axial lengths, which may include head portions 110 of the same or similar axial lengths and anchor portions 130 with differing axial lengths. Alternatively, in another embodiment, the head portion 110 may, for example, be available in multiple axial lengths to correspond to the varying sizes of patient bones, and the axial lengths of the anchor portion 130 may remain constant. In this way, a system or kit according to the present disclosure may include a plurality of implants 100 of differing total axial lengths, which may include anchor portions 130 of the same or similar axial lengths and head portions 110 with differing axial lengths. In yet another embodiment, both the head portion 110 and the anchor portion 130 may be available in multiple axial lengths to allow for selection based on the size of a patient's bones. In this way, a system or kit according to the present disclosure may include a plurality of implants 100 of differing total axial lengths, which may include head portions 110 with differing axial lengths and/or anchor portions 130 with differing axial lengths.

As shown in FIGS. 1-13 and 19-25 the head portion 110 includes a shaft portion 116 with a head or button 112 at a proximal first end and a breakaway coupling portion 122 at a distal second end. The head 112 may include a tool engagement opening 114 positioned at a free axial end thereof (and thereby of the head portion 110). The tool engagement opening 114 may have a non-circular cross-section such as, for example, a multi-lobed shape as shown in FIGS. 2, 5, 20 and 21, although other non-circular shapes are also contemplated (e.g., a hexagonal shape or a hexalobular drive feature). The tool engagement opening 114 having an irregular or non-circular cross-sectional shape may correspond in size and shape to a tool that can thereby mate therein and apply a torque to the implant 100 to rotate the implant 100 about its longitudinal axis. The engagement opening 114 may include or be a portion of the through hole, aperture or cannulation (or cannulated opening) 152 of head portion 110. The cannulated opening 152 of head portion 110 may form or comprise a portion of the cannulated opening or axial through hole 120 of the implant 100 (when the head portion 110 is assembled with the anchor portion 130).

Figure 6:
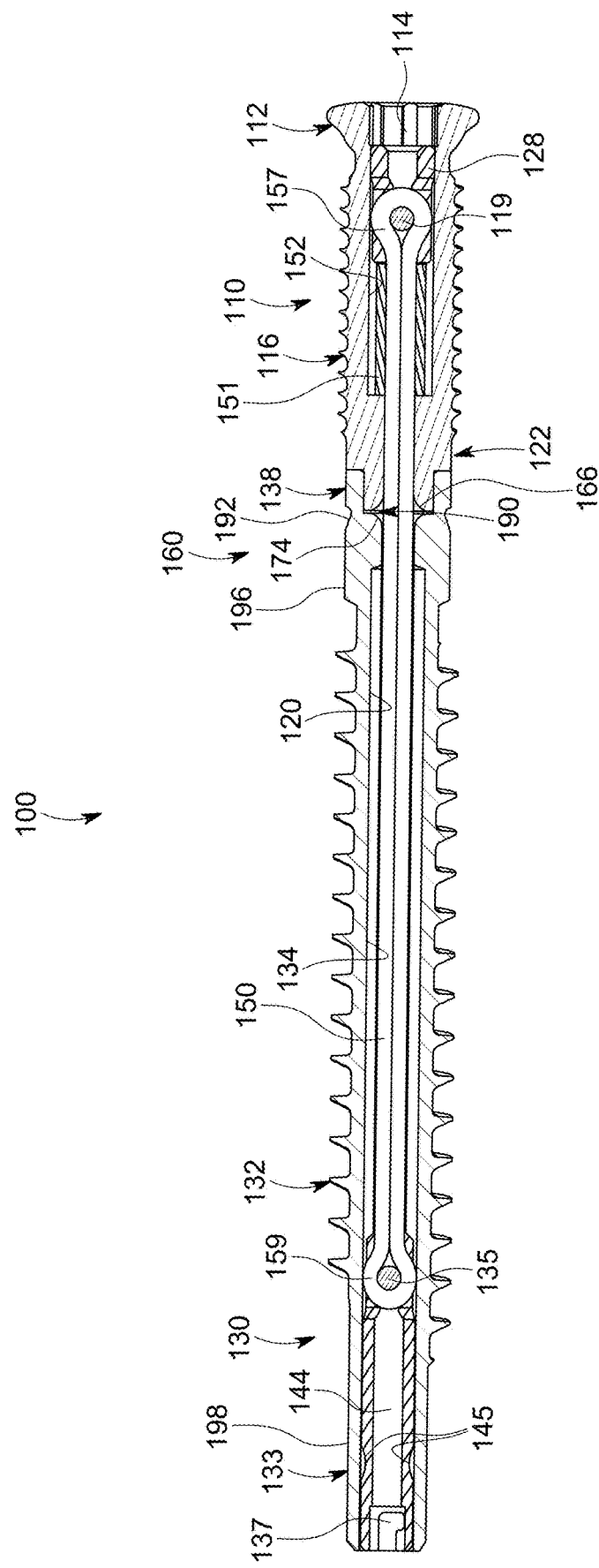
FIG. 6 illustrates a side cross-sectional view of the implant of FIG. 1, in accordance with an aspect of the present disclosure.
Figure 21:
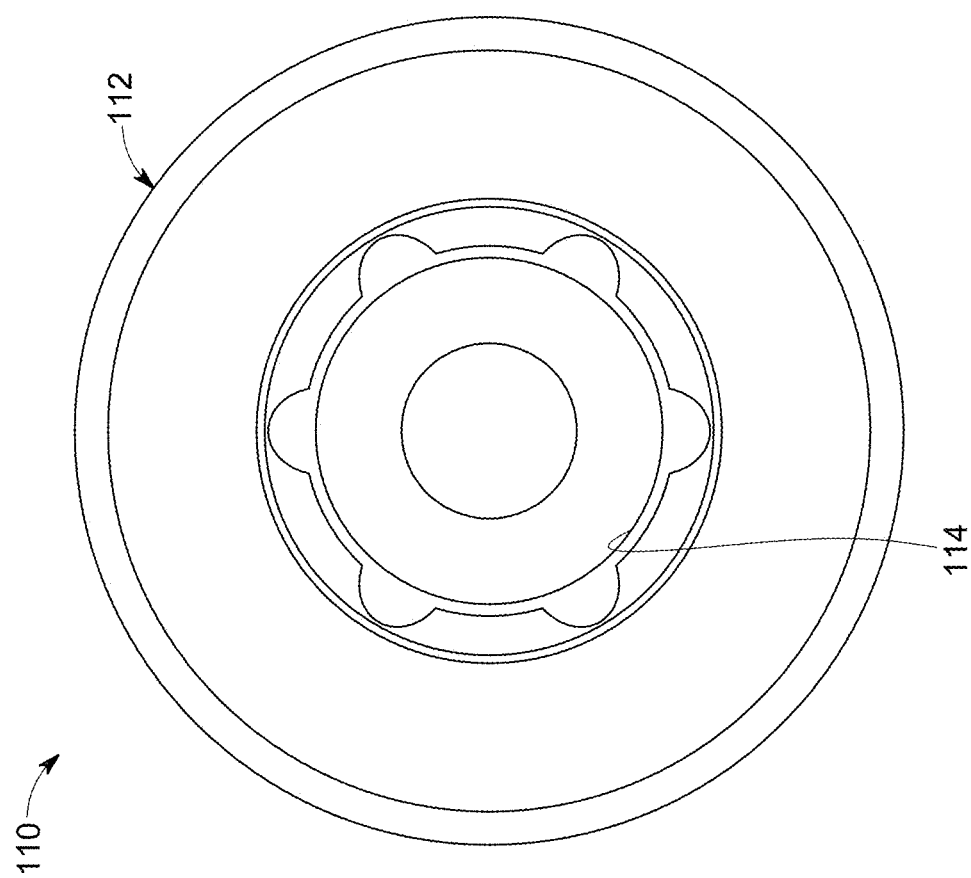
FIG. 21 illustrates an end view of the head portion of FIG. 19, in accordance with an aspect of the present disclosure.
Figure 22:
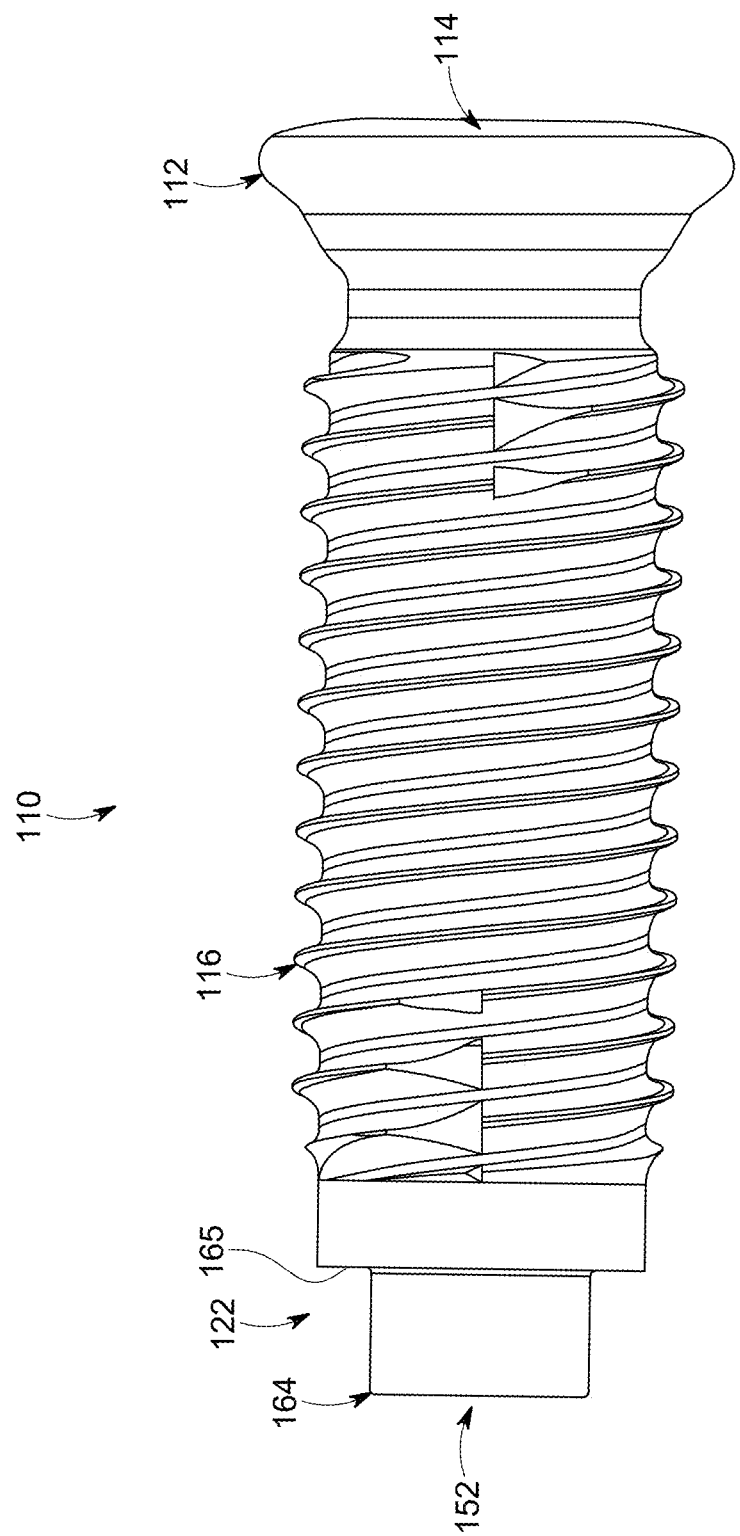
FIG. 22 illustrates a side view of the head portion of FIG. 19, in accordance with an aspect of the present disclosure.
Figure 23:
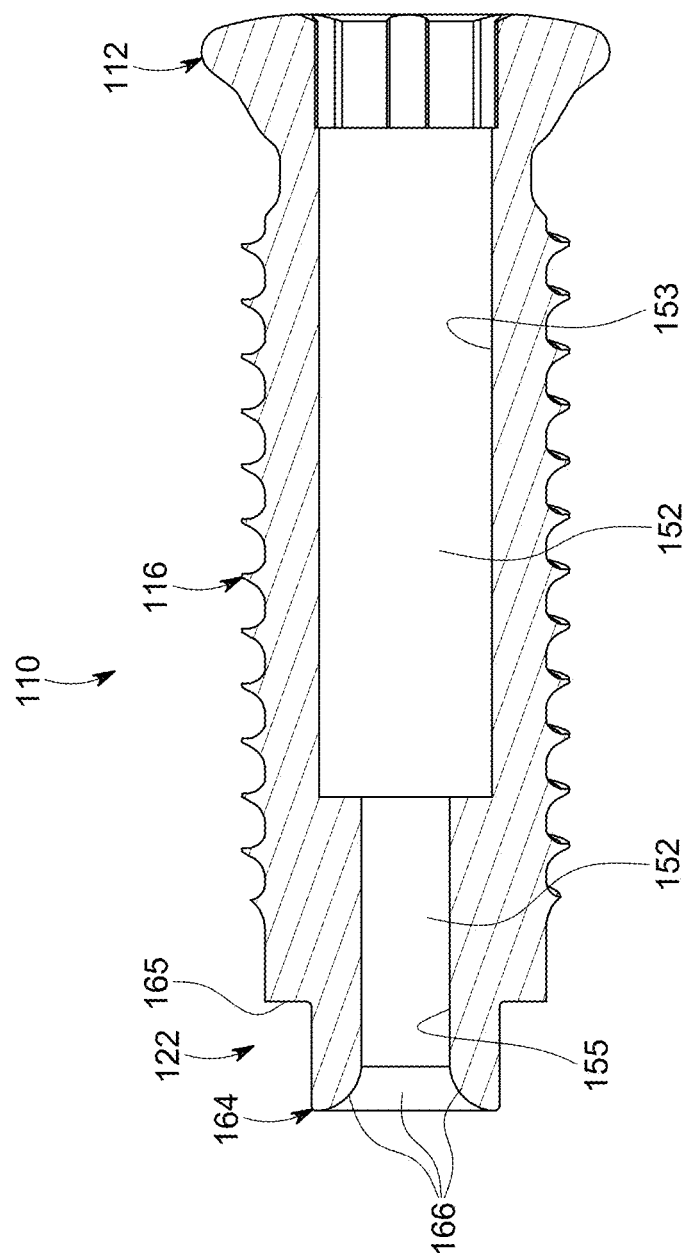
FIG. 23 illustrates a side cross-sectional view of the head portion of FIG. 19, in accordance with an aspect of the present disclosure.
Figure 24:
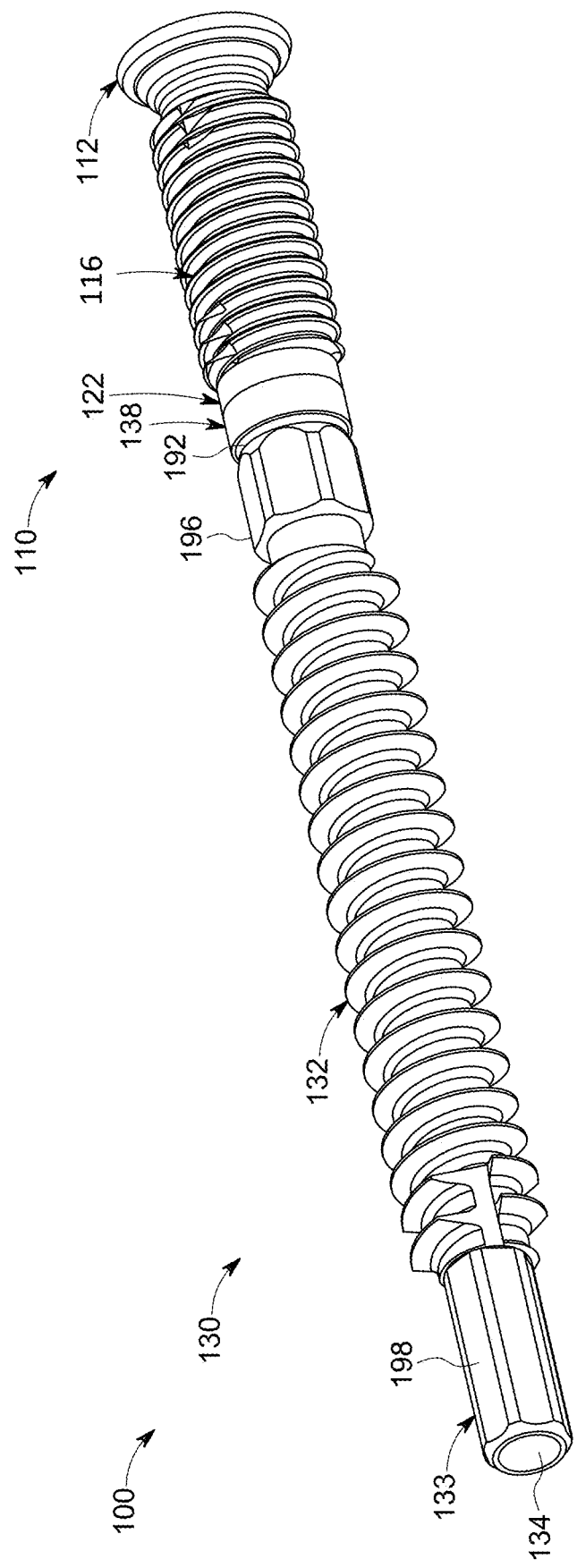
FIG. 24 illustrates a perspective view of an assembly of the exemplary anchor and head portions of the implant of FIG. 1, in accordance with an aspect of the present disclosure.

The shaft portion 116 may include external threads, and 19-25 and the through hole, aperture or cannulation 120, as shown in FIGS. 1-13. The cannulated opening 120 may extend through the entire shaft portion 116, and potentially the entire head portion 110, along the longitudinal axis of the head portion 110, as shown in FIGS. 6, 01 and 21. As noted above, the cannulated opening 120 may extend through the head 112 and be in communication with the tool engagement opening 114 (i.e., the tool engagement opening 114 may be a portion of the cannulated opening 120 of the head portion 110).

As shown in FIGS. 6, 7, 9-13, 19, 22 and 23, the breakaway coupling portion 122 may include an axially-extending coupling projection or tip 164 at the second end of the head portion 110. In some embodiments, the coupling projection 164 may be cylindrical (e.g., define a cylindrical outer surface). The cannulated opening 120 extends through the breakaway coupling portion 122 and is thereby open at the free axial end thereof, as shown in FIGS. 6, 7, 9-13, 19, 22 and 23, As also shown in FIGS. 6, 7, 9-13, 19, 22 and 23, the breakaway coupling portion 122 may further include an outer collar or stop surface 165 at a proximal end of the coupling projection 164. The outer collar or stop surface 165 may extend radially-outwardly from the exterior surface of the coupling projection 164, and may be substantially circumferential and/or planar.

As shown in FIGS. 6, 7, 9-13, 19, 22 and 23, the coupling projection 164 may include or define an internal end surface portion 166 that defines a distal end portion of the cannulated opening 120 at the free axial end of the breakaway coupling portion 122 (and the head portion 110 as a whole). As explained further below, the internal end surface portion 166 may cooperate with an internal end surface portion 174 of the anchor portion 130 to form an internal circumferential groove 190 within the cannulated opening 120 of the implant 100, as shown in FIGS. 6, 7, 9, 10 and 25. As shown in FIGS. 6, 7, 9-13, 19, 22 and 23, the internal end surface portion 166 of the coupling projection 164 may extend radially outwardly as it extends axially to or toward the proximal end of the coupling projection 164. In some embodiments, the internal end surface portion 166 of the coupling projection 164 extends from the internal surface portion of the coupling projection 164/shaft portion 116 to the outer surface of the coupling projection 164.

As shown in FIGS. 6, 7, 9-13, 19, 22 and 23, in some embodiments, the internal end surface portion 166 of the coupling projection 164 may arcuately extend radially outwardly and axially to or toward the proximal end of the coupling projection 164. The internal end surface portion 166 of the coupling projection 164 may thereby comprise an arcuately convex surface portion. For example, the internal end surface portion 166 may be defined by at least one radius. In some other embodiments (not shown), the internal end surface portion 166 of the coupling projection 164 may linearly extend radially outwardly and axially to or toward the proximal end of the coupling projection 164. For example, the internal end surface portion 166 may be defined by at least one planar or linear beveled surface. In some other embodiments (not shown), the internal end surface portion 166 of the coupling projection 164 may linearly and arcuately extend radially outwardly and axially to or toward the proximal end of the coupling projection 164. For example, the internal end surface portion 166 may be defined by at least one planar or linear beveled surface portion and at least one arcuate surface portion defined by at least one radius.

Figure 7:
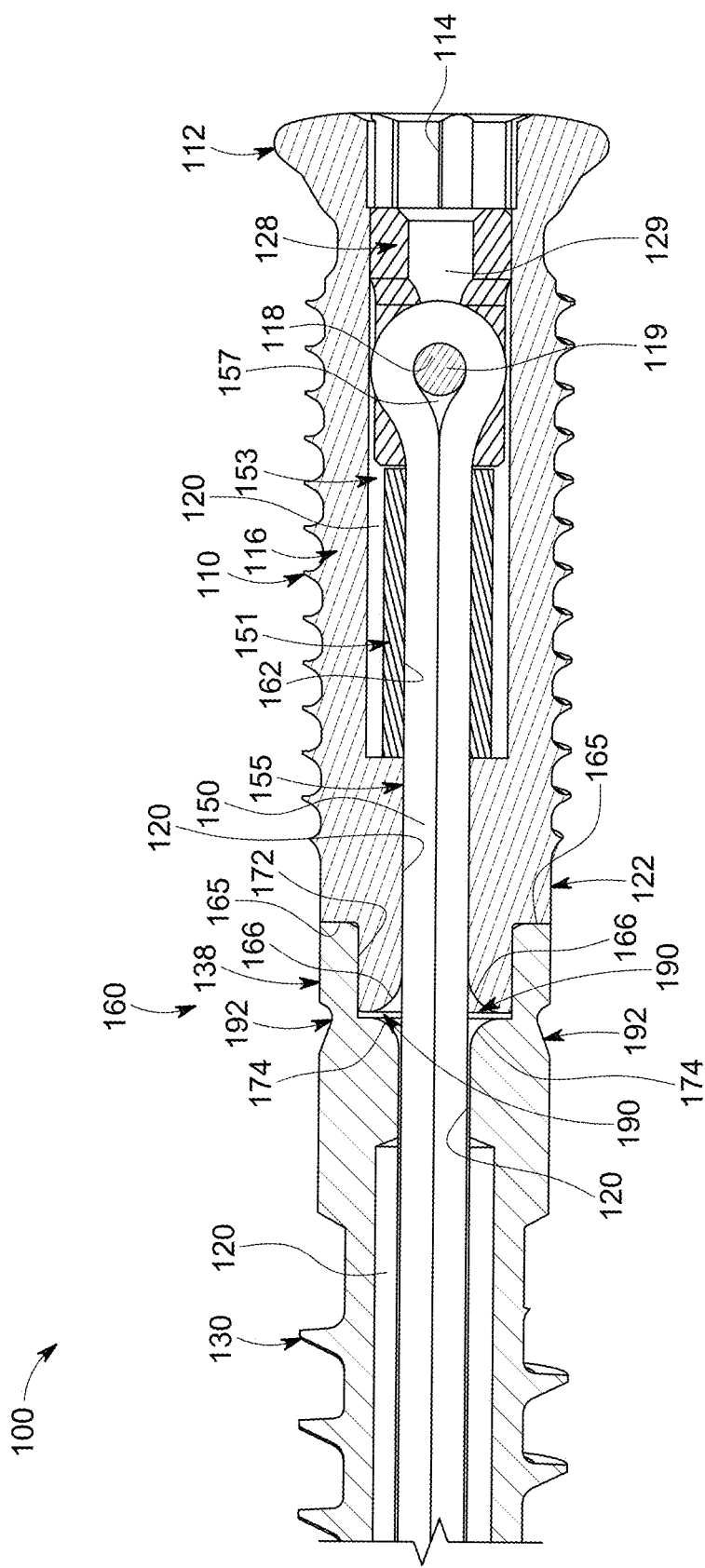
FIG. 7 illustrates a side cross-sectional view of a portion of the implant of FIG. 1, in accordance with an aspect of the present disclosure.
Figure 10:
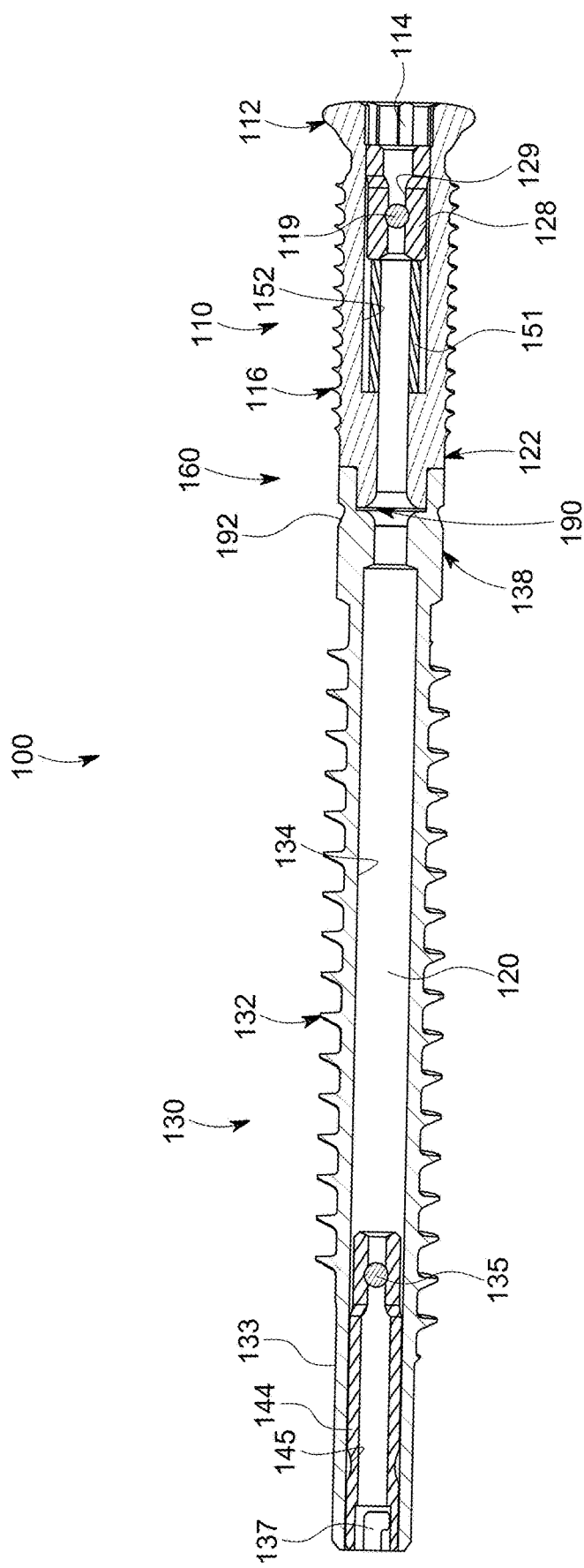
FIG. 10 illustrates a side cross-sectional view of the implant of FIG. 1 with a tension member thereof removed, in accordance with an aspect of the present disclosure.
Figure 11:
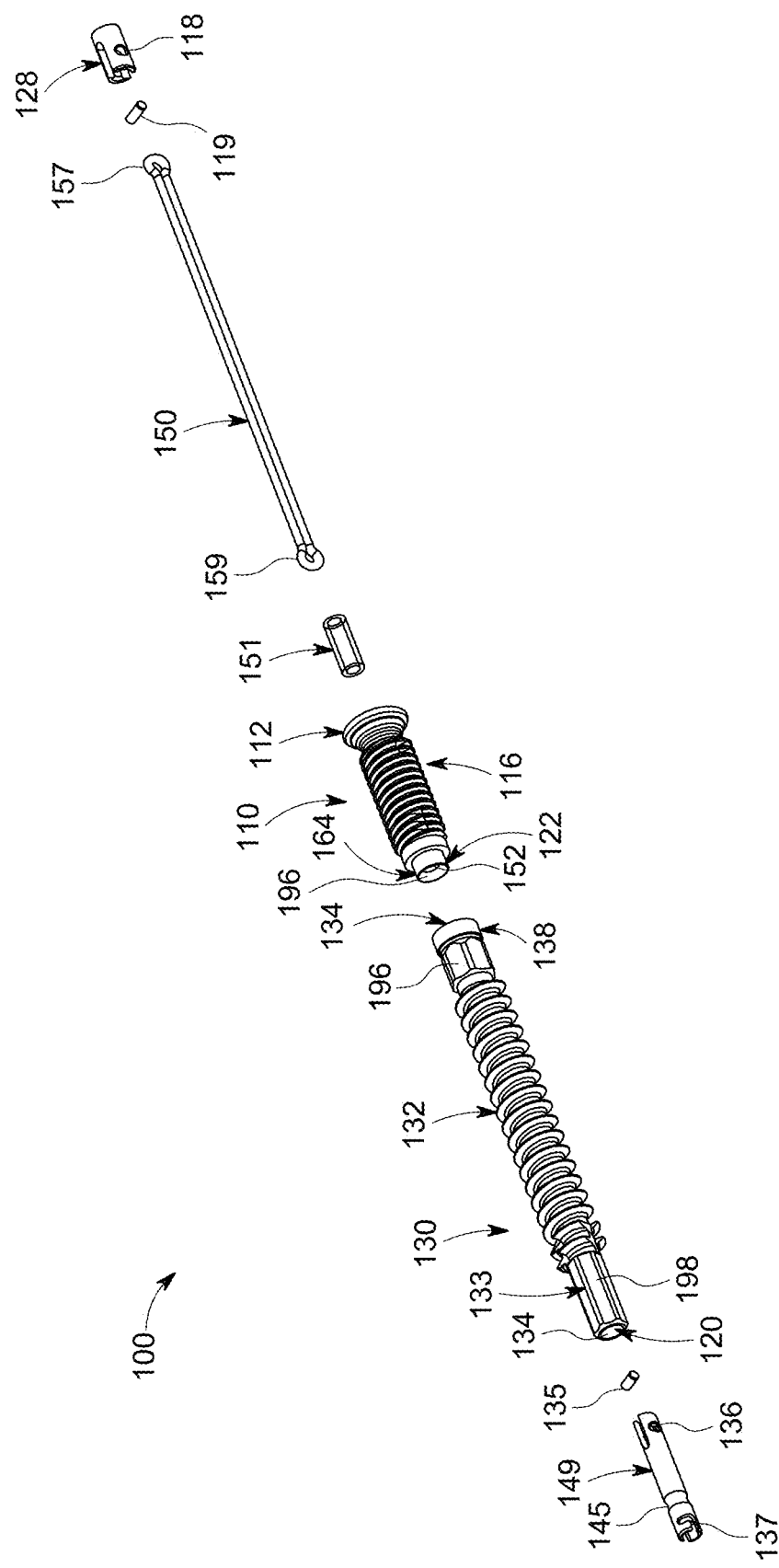
FIG. 11 illustrates a perspective exploded view of the implant of FIG. 1, in accordance with an aspect of the present disclosure.
Figure 12:
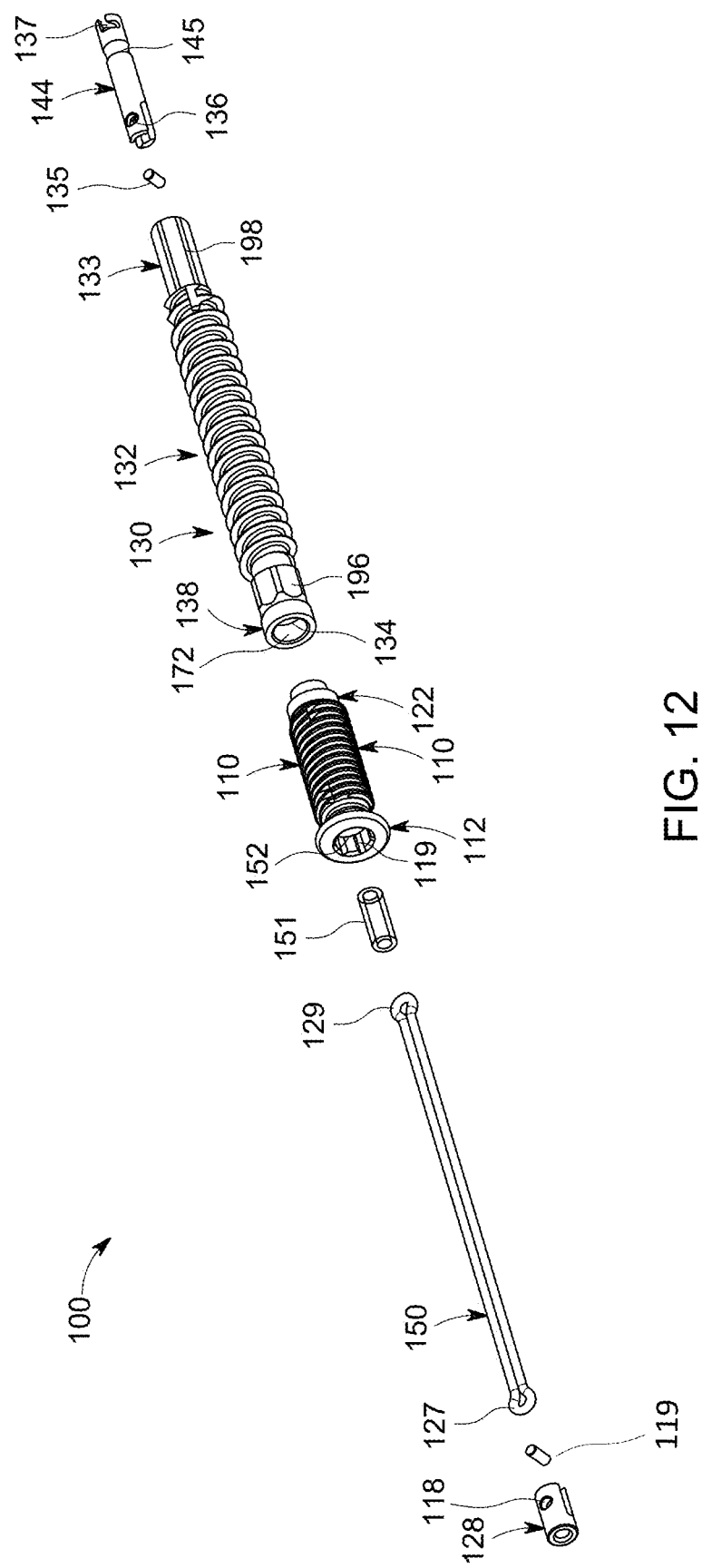
FIG. 12 illustrates another perspective exploded view of the implant of FIG. 1, in accordance with an aspect of the present disclosure.
Figure 13:
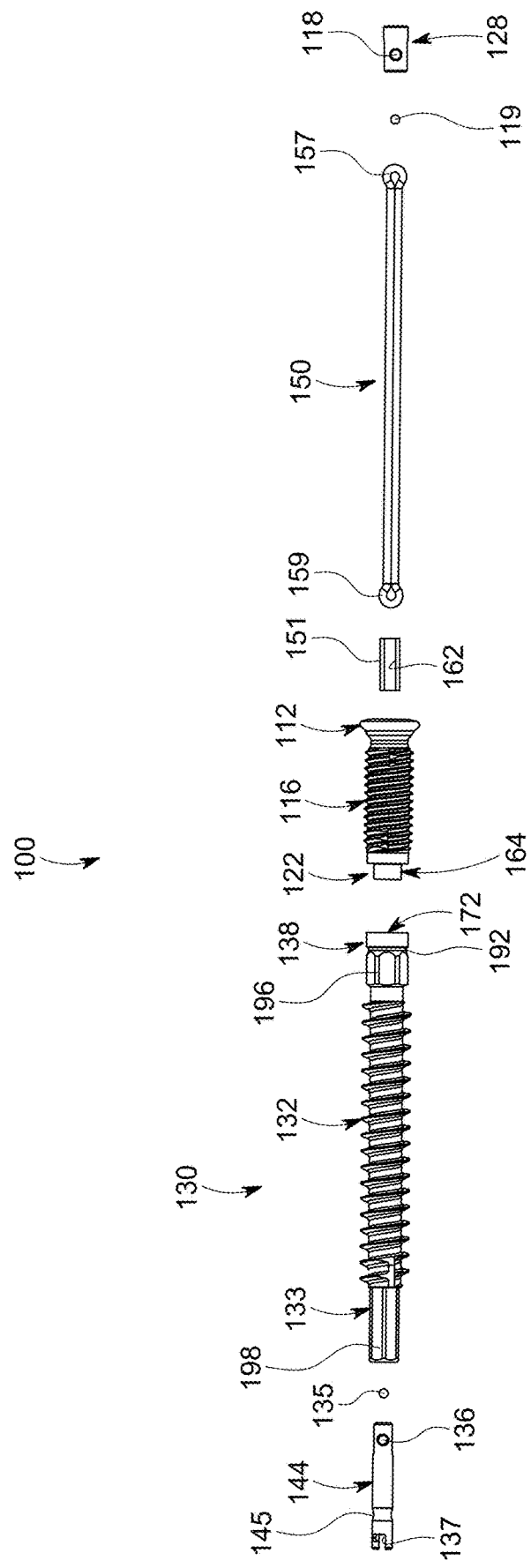
FIG. 13 illustrates a side exploded view of the implant of FIG. 1, in accordance with an aspect of the present disclosure.
Figure 14:
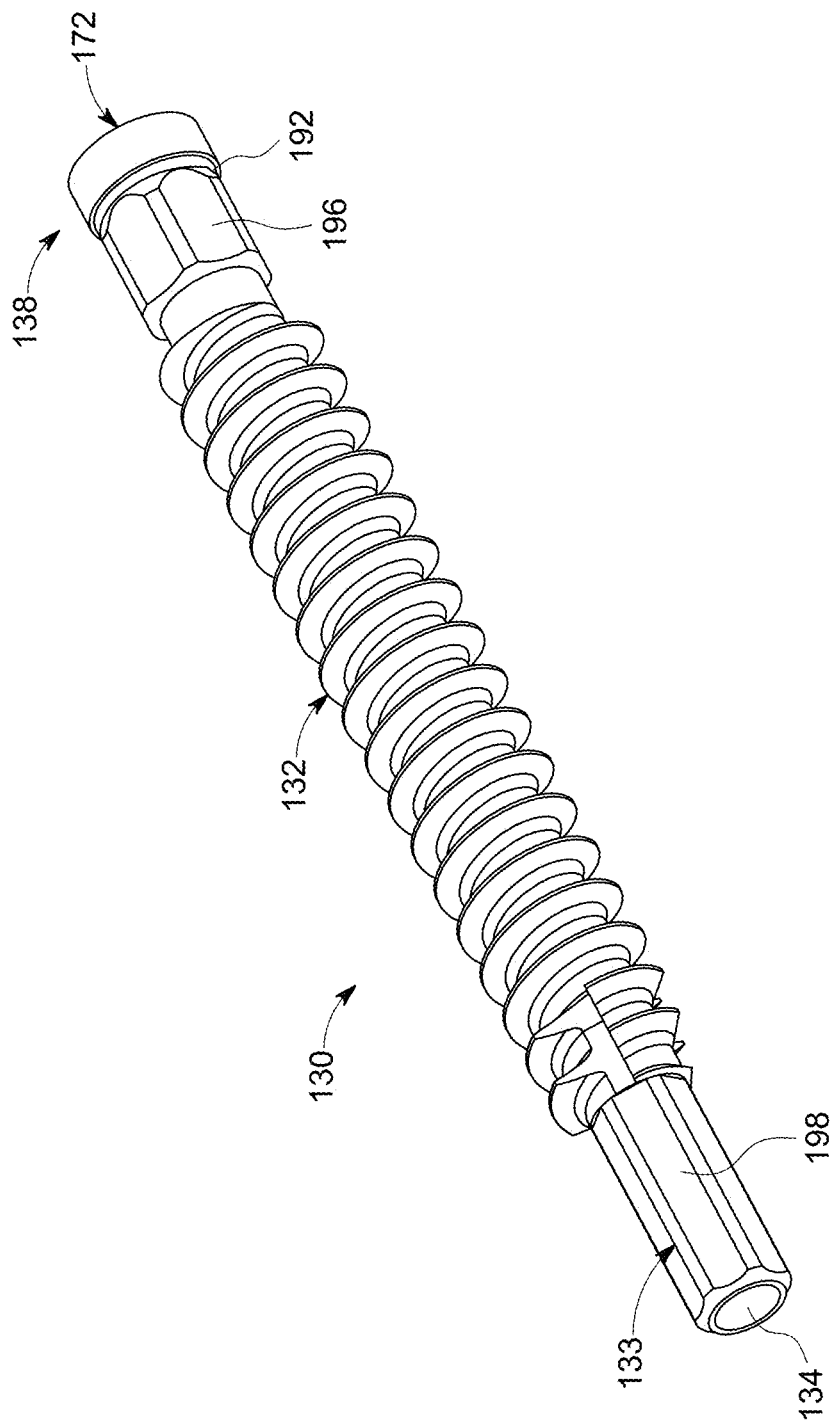
FIG. 14 illustrates a perspective view an exemplary anchor portion of the implant of FIG. 1, in accordance with an aspect of the present disclosure.
Figure 15:
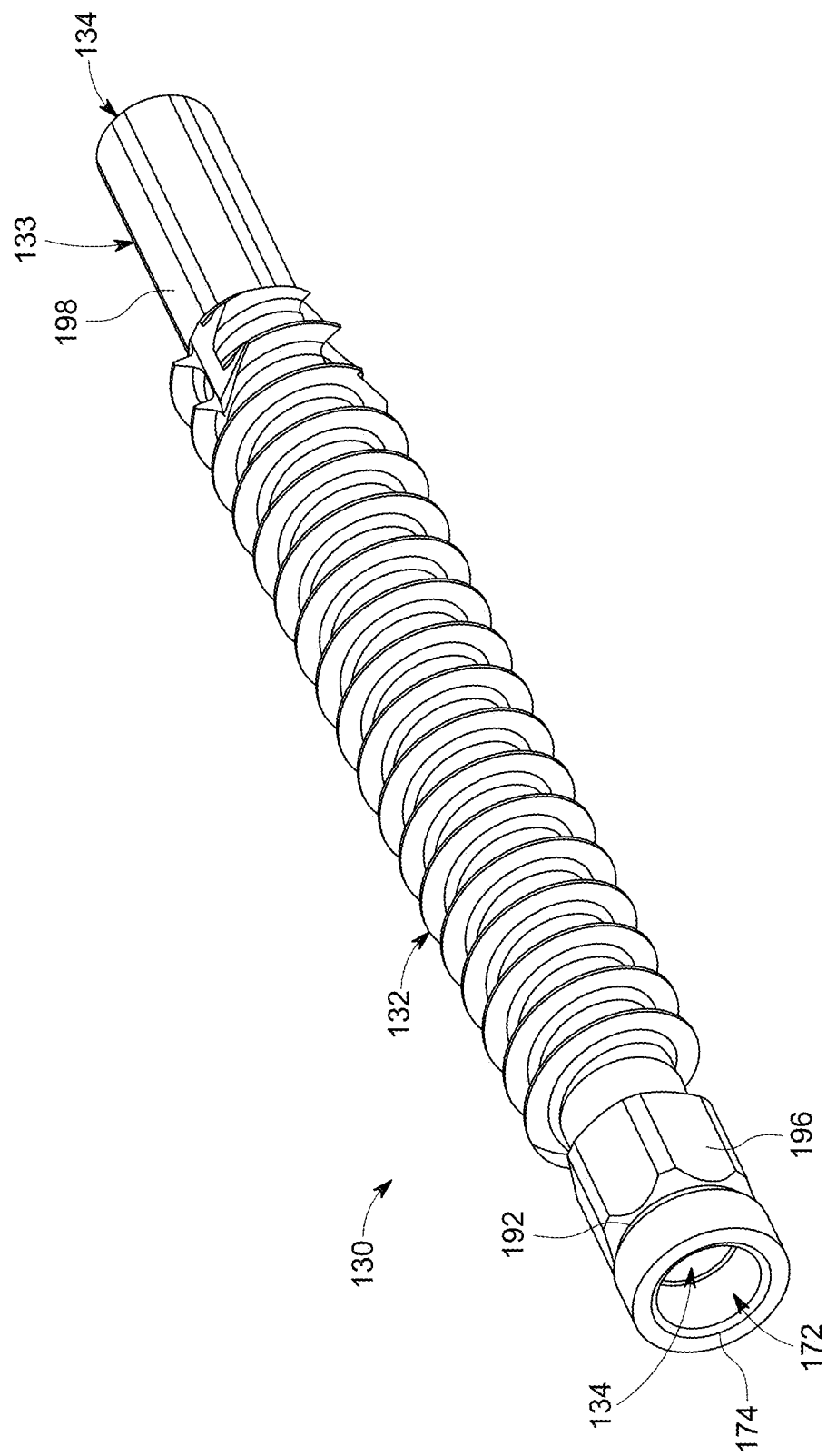
FIG. 15 illustrates another perspective view of the anchor portion of FIG. 14, in accordance with an aspect of the present disclosure.
Figure 16:
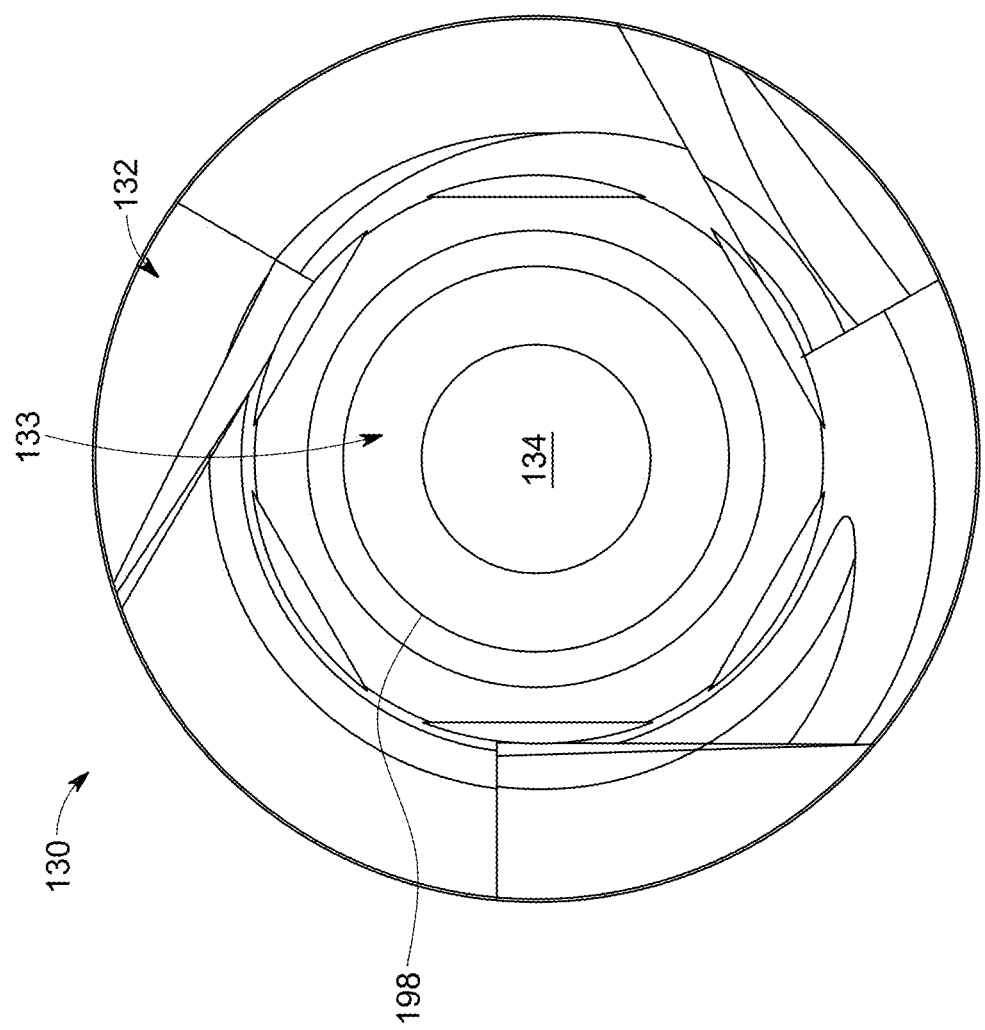
FIG. 16 illustrates an end view of the anchor portion of FIG. 14, in accordance with an aspect of the present disclosure.
Figure 17:
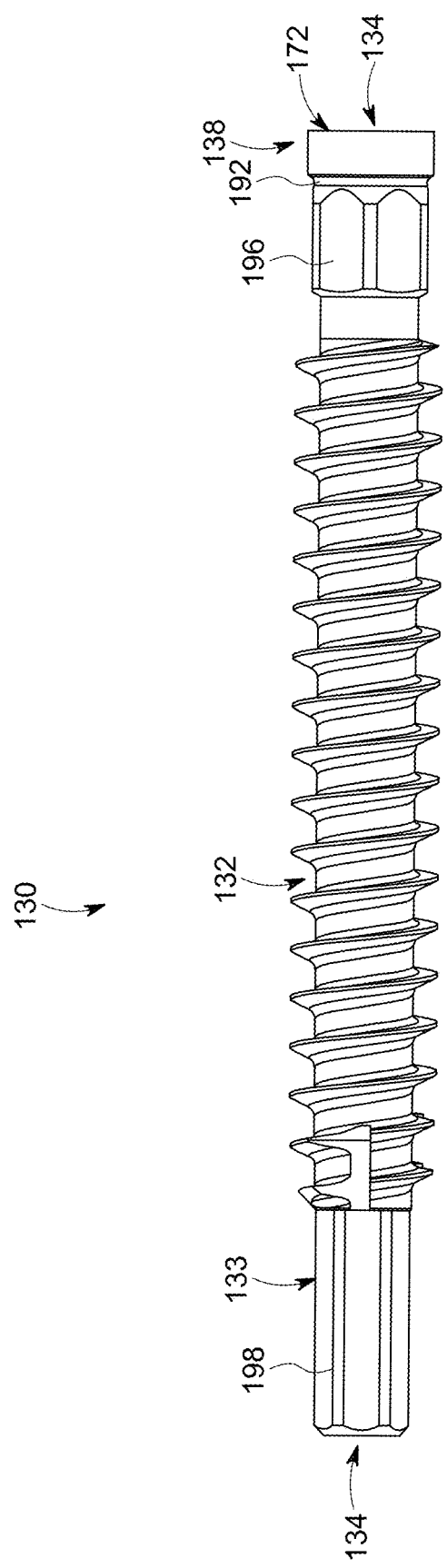
FIG. 17 illustrates a side view of the anchor portion of FIG. 14, in accordance with an aspect of the present disclosure.
Figure 18:
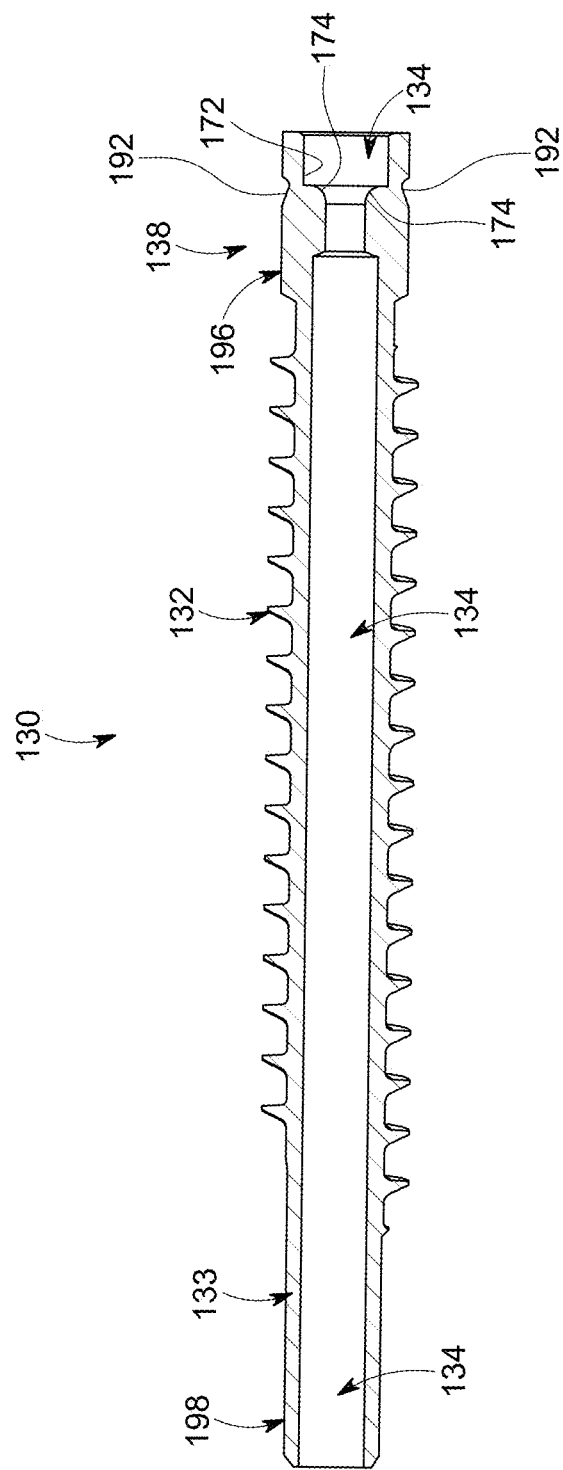
FIG. 18 illustrates a side cross-sectional view of the anchor portion of FIG. 14, in accordance with an aspect of the present disclosure.
Figure 19:
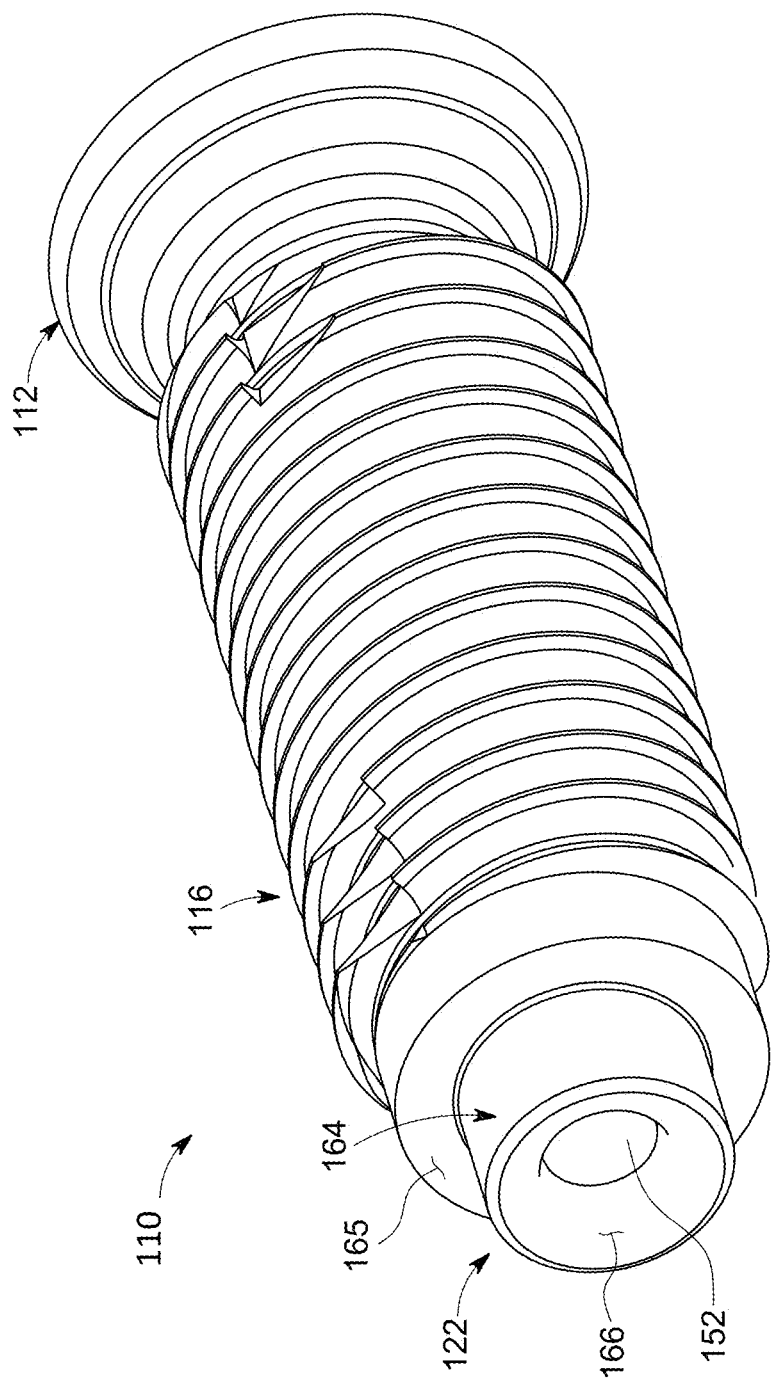
FIG. 19 illustrates a perspective view an exemplary head portion of the implant of FIG. 1, in accordance with an aspect of the present disclosure.
Figure 20:
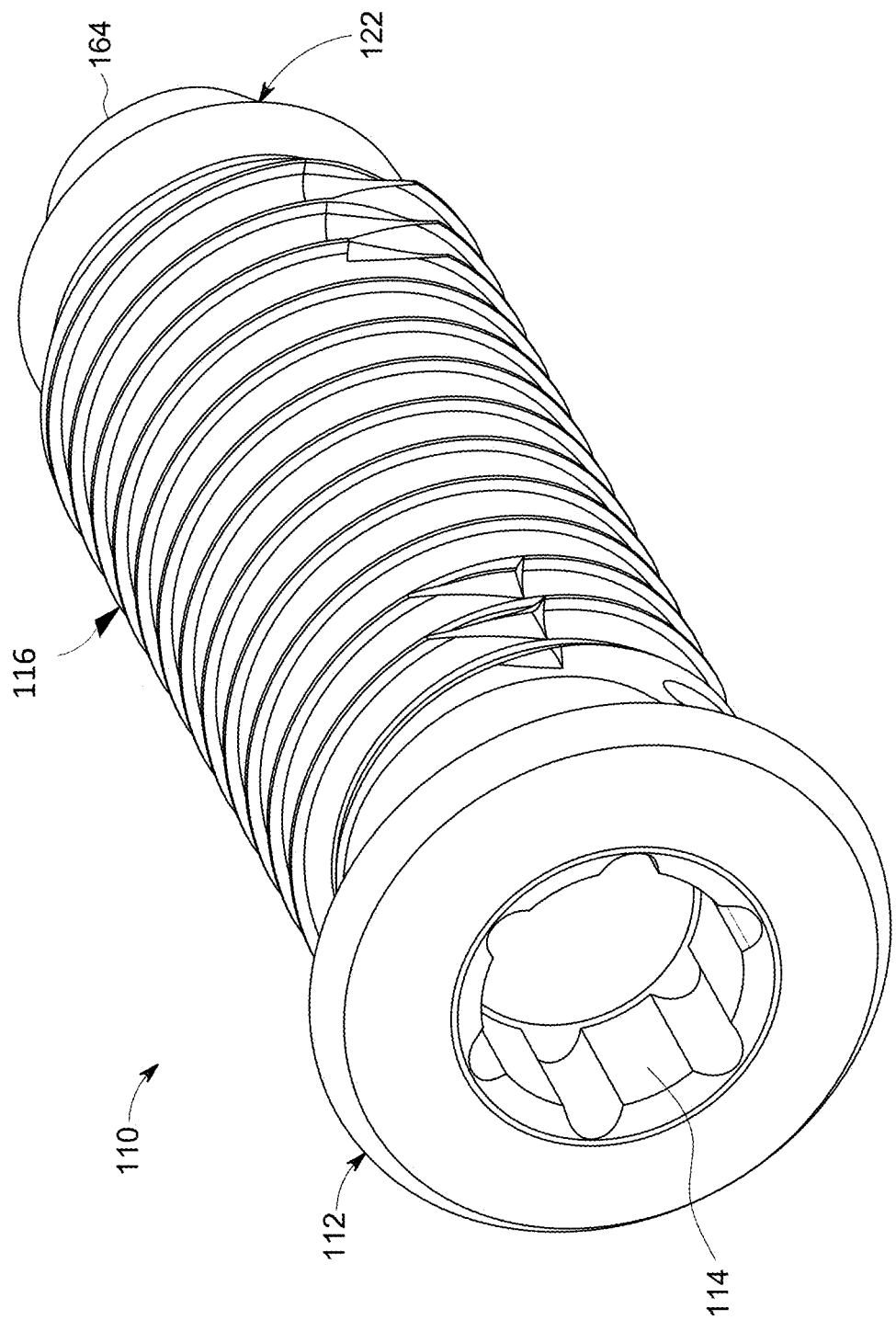
FIG. 20 illustrates another perspective view of the head portion of FIG. 19, in accordance with an aspect of the present disclosure.

The cannulated opening 152 of the head portion 110 is configured to allow a head post 128 of the implant 100 to be housed therein, and potentially axially slide or translate therein, as shown in FIGS. 6, 7 and 10. As shown in FIGS. 6, 7 and 10, the cannulated opening 152 of the head portion 110 includes a proximal enlarged portion 153 positioned proximate to the first end/head 112 and a reduced or narrow distal portion 155 positioned proximate to the second end/coupling projection 164 of the head portion 110. The enlarged portion 153 of the cannulated opening 152 of the head portion 110 is sized and shaped to contain or house the head post 128 and allow the head post 128 to axially travel therein, and also contain or house at least one tensioning member 151 positioned axially/longitudinally between the head post 128 and the narrow portion 155 of the cannulated opening 152. The at least one resilient member 151 may include a through hole 162, and the flexible constraint or tension member 150 may extend through the through hole 162 of the at least one resilient member 151 (e.g., the at least one resilient member 151 may extend about the constraint and/or tension member 150), as shown in FIGS. 6, 7, 10 and 35. For example, the at least one resilient member 151 may extend circumferentially about the constraint and/or tension member 150. The narrow portion 155 of the cannulated opening 152 is sized and shaped to allow the constraint and/or tension member 150 to axially pass therethrough, but to prevent the head post 128 and the at least one resilient member 151 from passing or translating (axially) therethrough.

The at least one resilient member 151, the narrow portion 155 of the cannulated opening 152 and/or the head post 128 are configured (e.g., sized and shaped) such that the at least one resilient member 151 is trapped or contained between the head post 128 and the narrow portion of the cannulated opening 152, as shown in FIGS. 6, 7, 10 and 35. In this way, when the constraint and/or tension member 150 is tensioned (as explained further below), the at least one resilient member 151 may be elastically compressed between the end of the enlarged portion 153 of the cannulated opening 152 of the head portion 110 and the head post 128. The at least one resilient member 151 may thereby apply a compressive force that pulls the anchor portion 130 and the head portion 110 together after the breakaway portion 160 of the implant 100 breaks/fractures, and/or allows a limited degree of relative axial translation or movement between the anchor portion 130 and the head portion 110.

In some embodiments, the at least one resilient member 151 may be comprised of one or more elastically deformable member or material. For example, the at least one resilient member 151 may be one or more springs (e.g., disc or coil spring) or elastically compressible disc or tube, or a combination thereof. For example, the at least one resilient member 151 may comprise an elastically compressible disc (e.g., elastomeric, polymer, polyurethane or polyethylene disc), tube (e.g., a polyurethane tube) or coil spring. In some embodiments, the at least one resilient member 151 comprises at least one urethane tube or like member, such as at least one polycarbonate urethane (PCU) tube or like member or at least one thermoplastic polyurethane (TPU) tube or like member. In some such embodiments, the at least one resilient member 151 may comprise a 75 A durometer, 85 A durometer or 95 A durometer urethane tube or like member.

In some embodiments, the at least one resilient member 151 may be made of, for example, an extruded thermoplastic urethane (TPU) with a durometer of, for example, 75-95 Shore A. In some embodiments, the at least one resilient member 151 may have an outer width or diameter of, for example, about 1.5 mm. The inner width or diameter of the through hole 162 of the at least one resilient member 151 may vary, such as based at least in part on the desired stiffness of the resilient member 151. In some embodiments, the at least one resilient member 151 may have a length of, for example, about 3 mm.

The at least one resilient member 151 is configured such that it elastically deforms to tension the constraint and/or tension member 150 so that it applies a compressive force (via elastic deformation of the at least one resilient member 151) that pulls the anchor portion 130 and the head portion 110 together (before and/or after the breakaway portion 160 of the implant 100 breaks/fractures), and/or allows a limited degree of relative axial translation or movement between the anchor portion 130 and the head portion 110 (after the breakaway portion 160 of the implant 100 breaks/fractures). The at least one resilient member 151 can provide assembly tension that maintains the anchor portion 130 and the head portion 110 together prior to welding thereof (as explained further below) and an in situ tension after implantation and fracture of the breakaway portion 160 of the implant 100 to resist anatomical forces, such as syndesmotic forces. For example, if the implant 100 is implanted into a fibula and a tibia with the breakaway portion 160 of the implant 100 at least partially positioned within the lateral gutter thereof, the in situ tension provided at least partially by the at least one resilient member 151 allows or provides for a recoverable diastatic motion of the fibula relative to the tibia, acting to release, absorb and/or dissipate pressure spikes in the lateral gutter, for example. In some embodiments, the at least one resilient member 151 may be elastically deformed such that the assembly tension maintains the components of the implant 100 mated together, and the at least one resilient member 151 may not be elastically deformed (or only partially elastically deformed) so as to provide the in situ tension in response to the recoverable diastatic motion and pressure spikes.

The anchor portion 130 may comprise a shaft portion 132 with a breakaway coupling portion 138 at a proximal first end portion and a crimp portion 133 at a distal second end portion, as shown in FIGS. 1-1-18, 24 and 25. The shaft portion 132 may be, for example, threaded along a portion of the shaft, such as a portion extending from or proximate to the breakaway coupling portion 138 to the crimp portion 133. A distal end portion of the threads of the anchor portion 130 proximate to the second end of the anchor portion may include at least one cutting element, for example, at least one flute (such as a cutting flute). The crimp portion 133 may be a non-threaded portion of the anchor portion 130 that extends from the threaded portion to distal free end of the anchor portion 130.

The anchor portion 130 also includes a through hole, aperture or cannulation (or cannulated opening) 134. The cannulated opening 134 of the anchor portion 130 may form or comprise a portion of the cannulated opening or axial through hole 120 of the implant 100 (when the anchor portion 130 is assembled with the head portion 110). The cannulated opening 134 may extend through the entire length of the anchor portion 130 along the longitudinal axis thereof, as shown in FIGS. 6, 9, 10, 18 and 25. As noted above, the cannulated opening 120 of the implant 100 may extend through the head 112 and be in communication with the tool engagement opening 114 (i.e., the tool engagement opening 114 may be a portion of the cannulated opening 120 of the head portion 110).

As shown in FIGS. 6, 7, 9, 10, 12, 15, 18 and 25, a proximal end portion of the breakaway coupling portion 138 may include a coupling cavity 172 configured to mate (e.g., interference fit) with the coupling projection 164 of the head portion 110. The coupling projection 164 of the head portion 110 may thereby be received within the coupling cavity 172 The configuration (e.g., size and shape) of the coupling cavity 172 may thereby substantially correspond to that of the coupling projection 164 of the head portion 110. The coupling cavity 172 may form or comprise an enlarged portion of the cannulated opening 134 of the anchor portion 130 proximally of a narrow portion of the cannulated opening 134 of the anchor portion 130, as shown in as shown in FIGS. 6, 9, 10, 18 and 25. The cannulated opening 134 extends through the breakaway coupling portion 164 and is thereby open at the free axial end thereof, as shown in FIGS. 6, 9, 10, 18 and 25.

As shown in FIGS. 6, 9, 10, 18 and 25, a distal bottom portion, end or surface 174 of the coupling cavity 172 of the breakaway coupling portion 138 of the anchor portion 130 defines or comprises an internal end surface portion of the anchor portion 130. As discussed above, the internal end surface portion 174 of the coupling cavity 172 of the anchor portion 130 cooperates with the internal end surface portion 166 of the breakaway coupling portion 122 of the head portion 110 to form an internal circumferential groove 190 within the cannulated opening 120 of the implant 100. The internal end surface portion 174 of the coupling cavity 172 may extend radially-outwardly from an outer internal surface portion of the enlarged portion of the coupling cavity 172 to an outer internal surface portion of the narrow portion of the coupling cavity 172 and may be substantially circumferential.

As shown in FIGS. FIGS. 6, 9, 10, 18 and 25, the internal end surface portion 174 of the coupling cavity 172 of the anchor portion 130 may extend radially inwardly as it extends axially to or toward the crimp portion 133 (from the enlarged portion to the narrow portion of the coupling cavity 172. In some embodiments, internal end surface portion 174 of the coupling cavity 172 extends from the distal end of the enlarged portion of the coupling cavity 172 to the proximal end of the narrow portion of the coupling cavity 172 as shown in FIGS. 6, 9, 10, 18 and 25.

As shown in FIGS. 6, 9, 10, 18 and 25, in some embodiment the internal end surface portion 174 of the coupling cavity 172 may arcuately extend radially outwardly and axially to or toward the crimp portion 133 (from the enlarged portion to the narrow portion of the coupling cavity 172. The internal end surface portion 174 of the coupling cavity 172 may thereby comprise an arcuately convex surface portion. For example, the internal end surface portion 174 of the coupling cavity 172 may be defined by at least one radius. In some other embodiments (not shown), the internal end surface portion 174 of the coupling cavity 172 may linearly extend radially outwardly and axially to or toward the crimp portion 133 (from the enlarged portion to the narrow portion of the coupling cavity 172 For example, the internal end surface portion 174 of the coupling cavity 172 may be defined by at least one planar or linear beveled surface. In some other embodiments (not shown), the internal end surface portion 174 of the coupling cavity 172 may linearly and arcuately extend radially outwardly and axially to or toward the crimp portion 133 (from the enlarged portion to the narrow portion of the coupling cavity 172 For example, the internal end surface portion of the coupling cavity 172 may be defined by at least one planar or linear beveled surface portion and at least one arcuate surface portion defined by at least one radius.

As shown in FIGS. 6, 7, 9, 10 and 25, the internal end surface portion 174 of the coupling cavity 172 of the breakaway coupling portion 138 of the anchor portion 130 cooperates with the internal end surface portion 166 of the coupling projection 164 of the breakaway coupling portion 122 of the head portion 110 to form an internal circumferential groove 190 within the cannulated opening 120 of the breakaway portion 160 of the implant 100. The internal circumferential groove 190 within the cannulated opening 120 of the breakaway portion 160 of the implant 100 may comprise, for example, a notch, groove, necking, or recess into the interior surface of the implant 100 that forms the cannulated opening 120 thereof. As the internal end surface portions 166, 174 may be arcuate/curved and/or flat/planar, the internal circumferential groove 190 of the breakaway portion 160 may have, for example, curved/arcuate/rounded and/or flat/planar sides. The bottom or deepest portion of the internal circumferential groove 190 of the breakaway portion 160 of the breakaway portion 160 may be arcuate or linear/straight.

As also shown in FIGS. 6, 7, 9, 10, 13-15, 17, 18, 25 and 25, the exterior surface of the proximal end portion of the breakaway coupling portion 138 (i.e., the exterior surface of the proximal end portion extending about and/or forming the coupling cavity 172) includes an external circumferential groove 192 that is axially aligned (i.e., extends about) the internal within the internal circumferential groove 190 in the cannulated opening 120 of the breakaway portion 160 of the implant 100. The external circumferential groove 192 of the breakaway portion 160 of the implant 100 may comprise, for example, a notch, groove, necking, or recess into the exterior surface of the breakaway portion 160 of the implant 100. The external circumferential groove 192 may have, for example, curved/arcuate/rounded and/or flat/planar sides. The bottom or deepest portion of the external circumferential groove 192 of the breakaway portion 160 may be arcuate or linear/straight.

As shown in FIGS. 6, 7, 9, 10 and 25, the coupling projection 164 of the breakaway coupling portion 122 of the head portion 110 may initially be freely assembled/positioned within the coupling cavity 172 of the breakaway coupling portion 138 of the anchor portion 130. In some embodiments the coupling projection 164 of the breakaway coupling portion 122 of the head portion 110 and the coupling cavity 172 of the breakaway coupling portion 138 of the anchor portion 130 such that they mate and include an interference fit.

The proximal end surface of the coupling cavity 172 of the breakaway coupling portion 138 of the anchor portion 130 may abut or be seated against the outer collar or stop surface 165 of the breakaway coupling portion 122 of the head portion 110, as shown in FIG. 7. In some other embodiments (not shown), the proximal end surface of the coupling cavity 172 of the breakaway coupling portion 138 of the anchor portion 130 may be axially spaced from the outer collar or stop surface 165 of the breakaway coupling portion 122 of the head portion 110. In some arrangements, the internal end surface portion 166 of the coupling projection 164 of the breakaway coupling portion 122 of the head portion 110 may be axially spaced from the internal end surface portion 174 of the coupling cavity 172 of the breakaway coupling portion 138 of the anchor portion 130, as shown in FIG. 7. In some other embodiments (not shown), the internal end surface portion 166 of the coupling projection 164 of the breakaway coupling portion 122 of the head portion 110 may abut the internal end surface portion 174 of the coupling cavity 172 of the breakaway coupling portion 138 of the anchor portion 130.

As shown in FIGS. 6, 7, 9 and 10, the constraint and/or tension member 150 may be an elongated structure or member that extends from or proximate to (and is affixed to) the crimp portion 133 of the anchor portion 130 and at least proximate to (and is affixed to) the shaft portion 116 and/or the head 112 of the head portion 110. In the exemplary illustrated embodiment of the implant 100, the constraint and/or tension member 150 comprises a suture, specifically a continuous suture loop. In one exemplary embodiment, the suture may comprise a size #0 suture. The constraint and/or tension member 150 may be of another configuration or structure. The constraint and/or tension member 150 may be, for example, a stranded cerclage cable or similar construct. The constraint and/or tension member 150 may also be made of, for example, titanium, stainless steel, polymers, polyester, polypropylene or UHMWPE suture, co-braids thereof, or a like material, as known by one of ordinary skill in the art. The constraint and/or tension member 150 may be, for example, a suture (e.g., a braided suture), such as a single cross-section strand of suture or multiple loops of suture. For example, the constraint and/or tension member 150 may be a UHMWPE and polypropylene co-braid suture. The constraint and/or tension member 150 may or may not be elastically axially/longitudinally stretchable or deformable.

Figure 25:
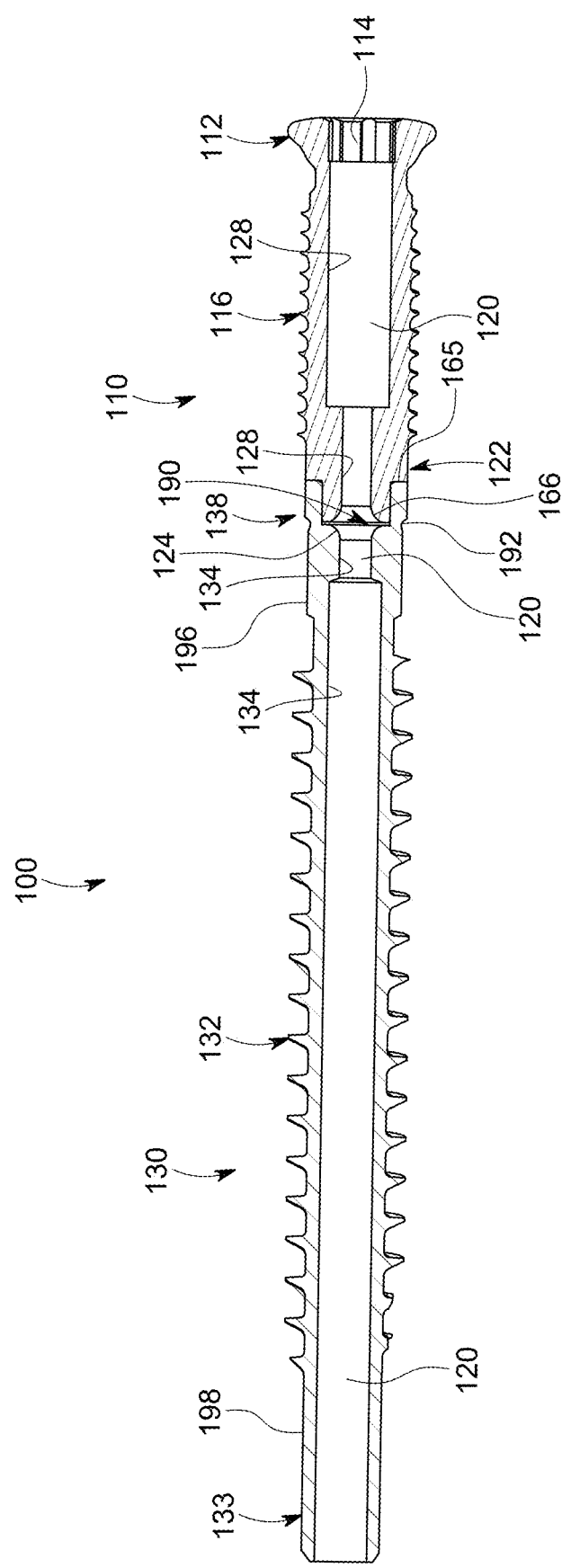
FIG. 25 illustrates a side cross-sectional view of the assembly of FIG. 24, in accordance with an aspect of the present disclosure.
Figure 26:
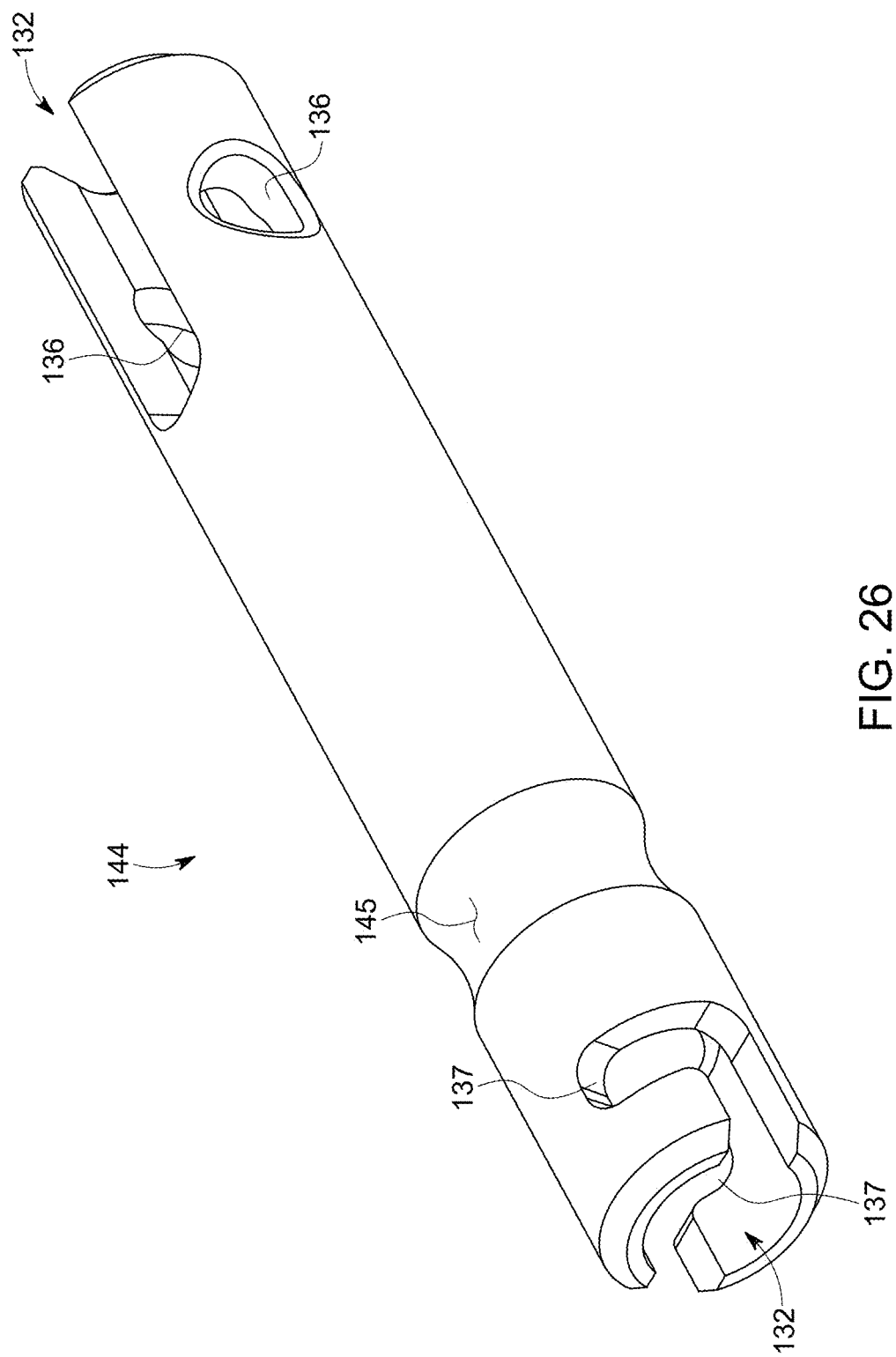
FIG. 26 illustrates a perspective view an exemplary tip post of the implant of FIG. 1, in accordance with an aspect of the present disclosure.
Figure 27:
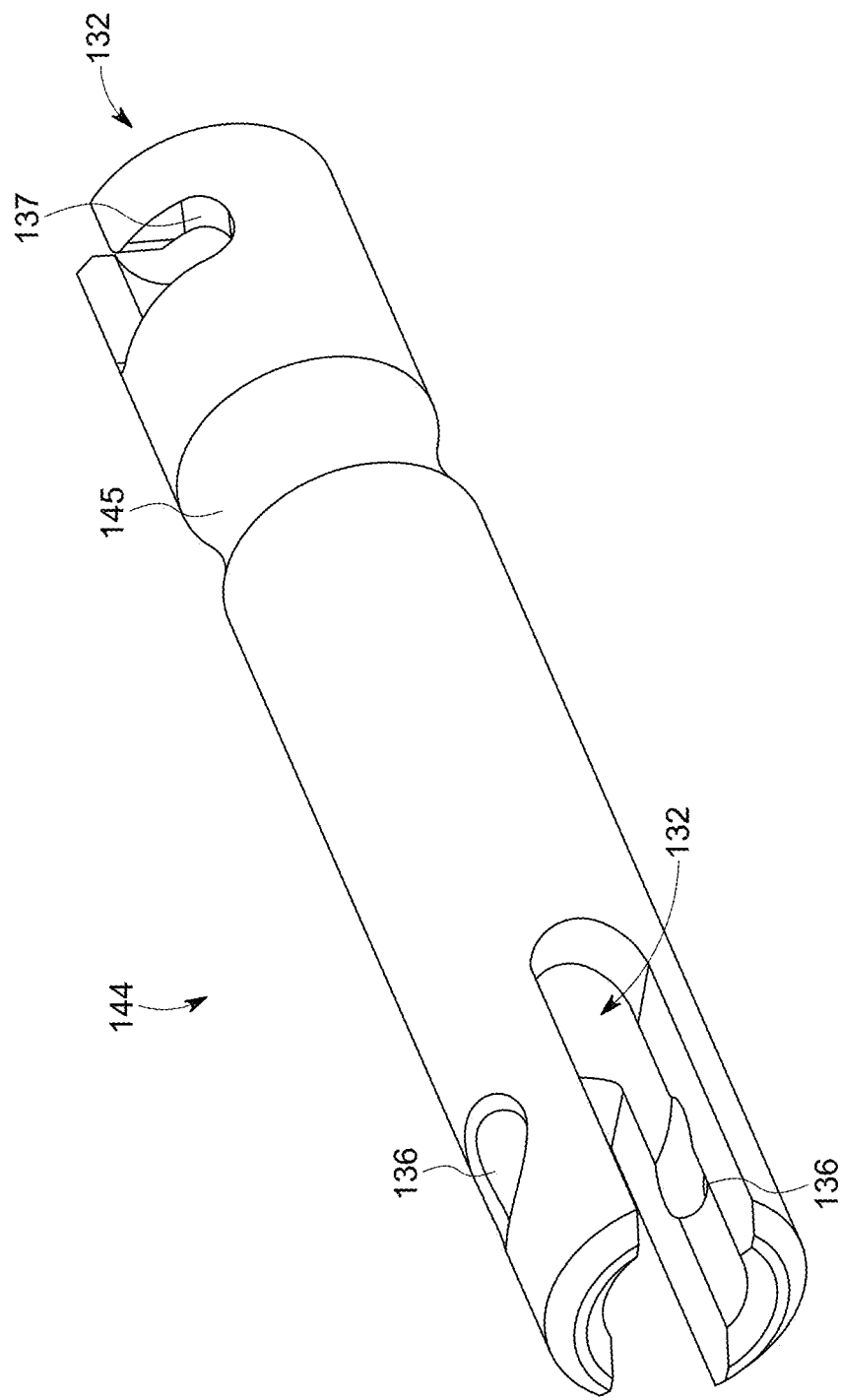
FIG. 27 illustrates another perspective view of the tip post of FIG. 26, in accordance with an aspect of the present disclosure.
Figure 28:
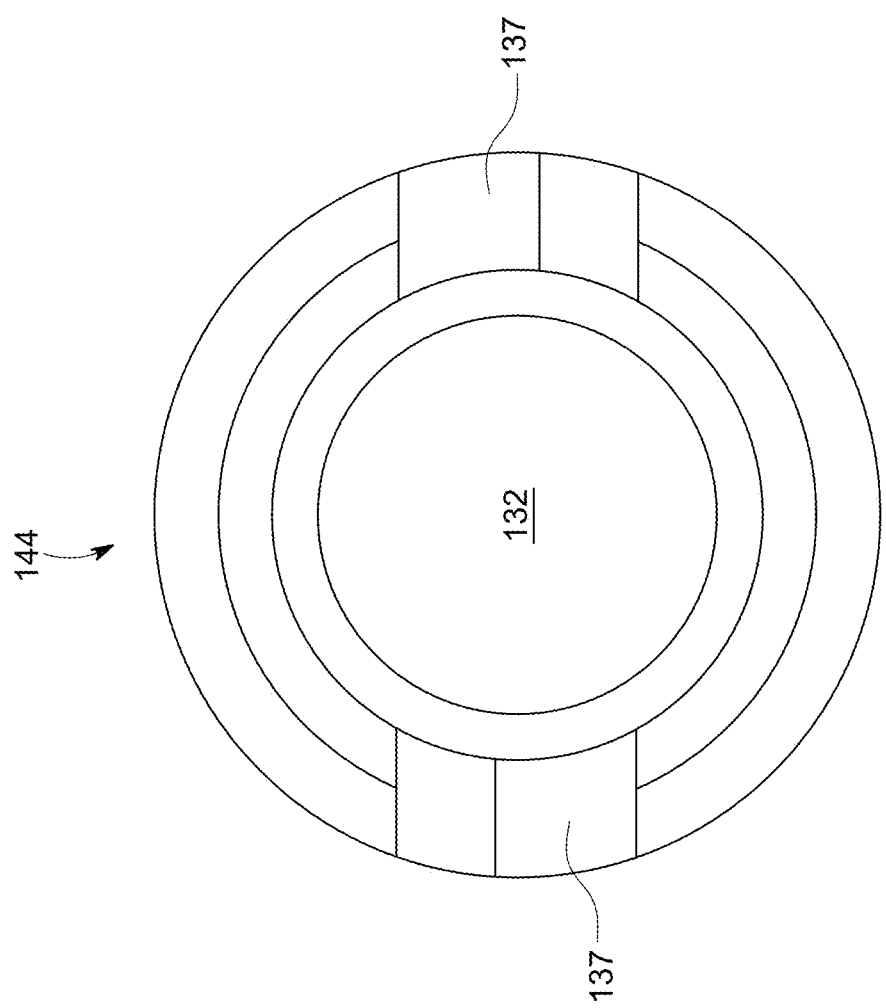
FIG. 28 illustrates an end view of the tip post of FIG. 26, in accordance with an aspect of the present disclosure.
Figure 29:
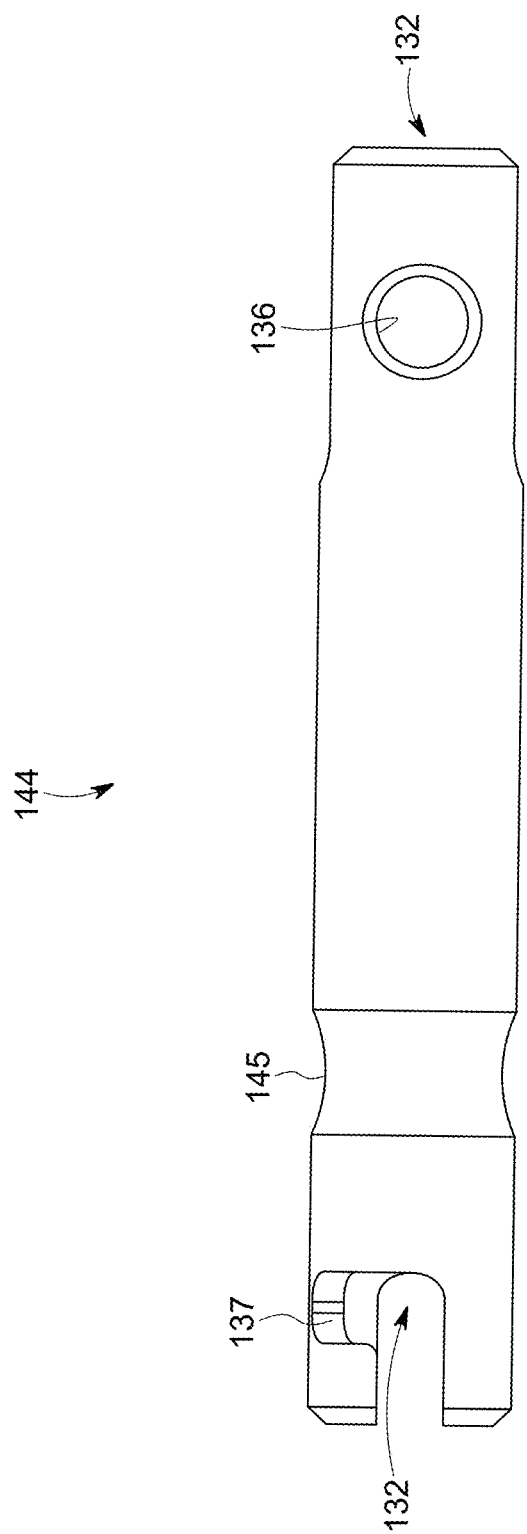
FIG. 29 illustrates a side view of the tip post of FIG. 26, in accordance with an aspect of the present disclosure.
Figure 30:
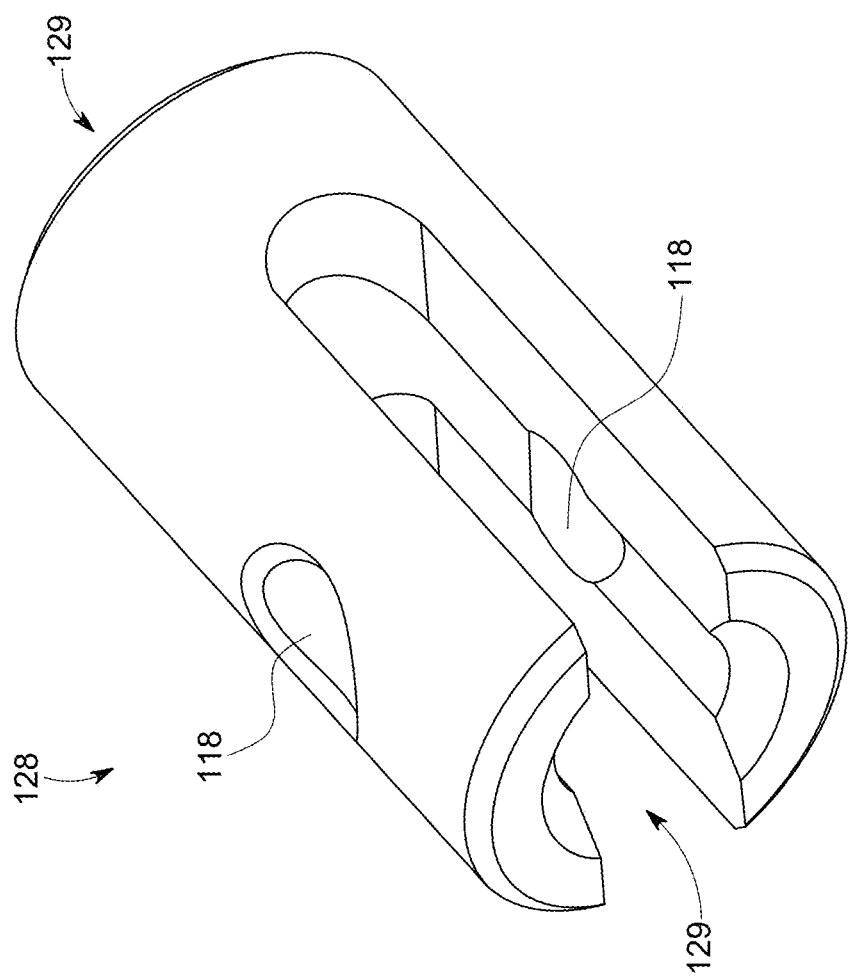
FIG. 30 illustrates a perspective view an exemplary head post of the implant of FIG. 1, in accordance with an aspect of the present disclosure.
Figure 31:
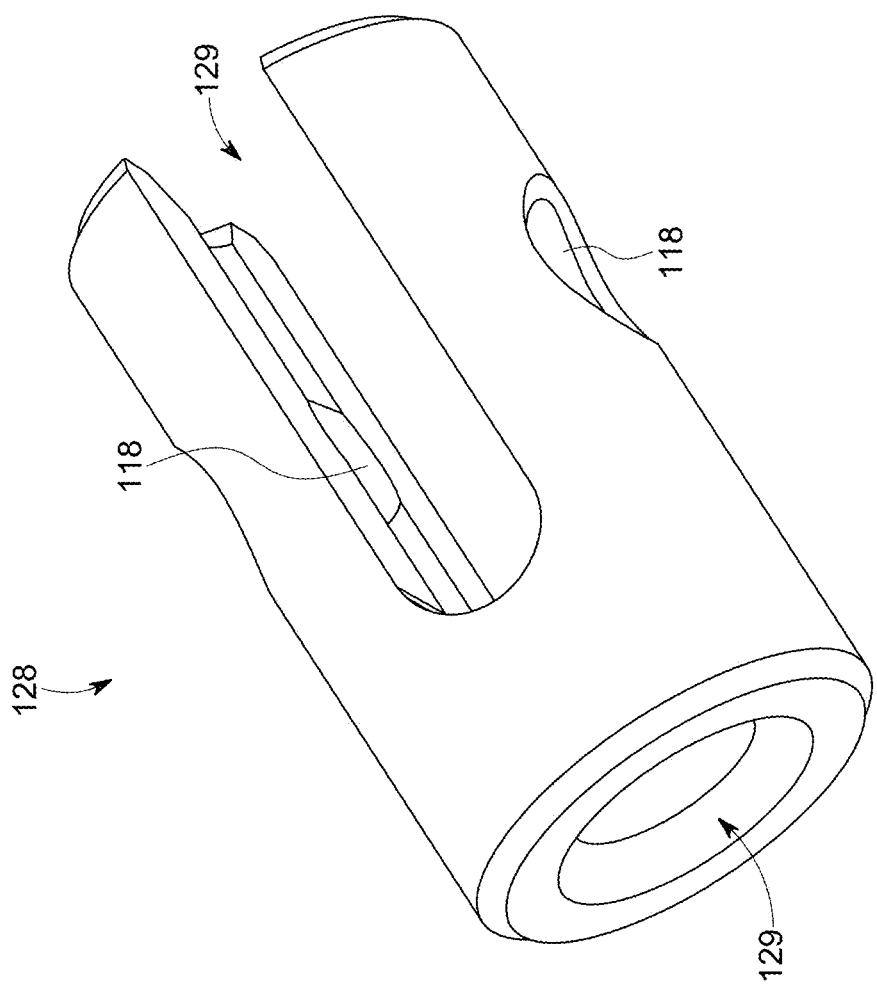
FIG. 31 illustrates another perspective view of the head post of FIG. 30, in accordance with an aspect of the present disclosure.
Figure 32:
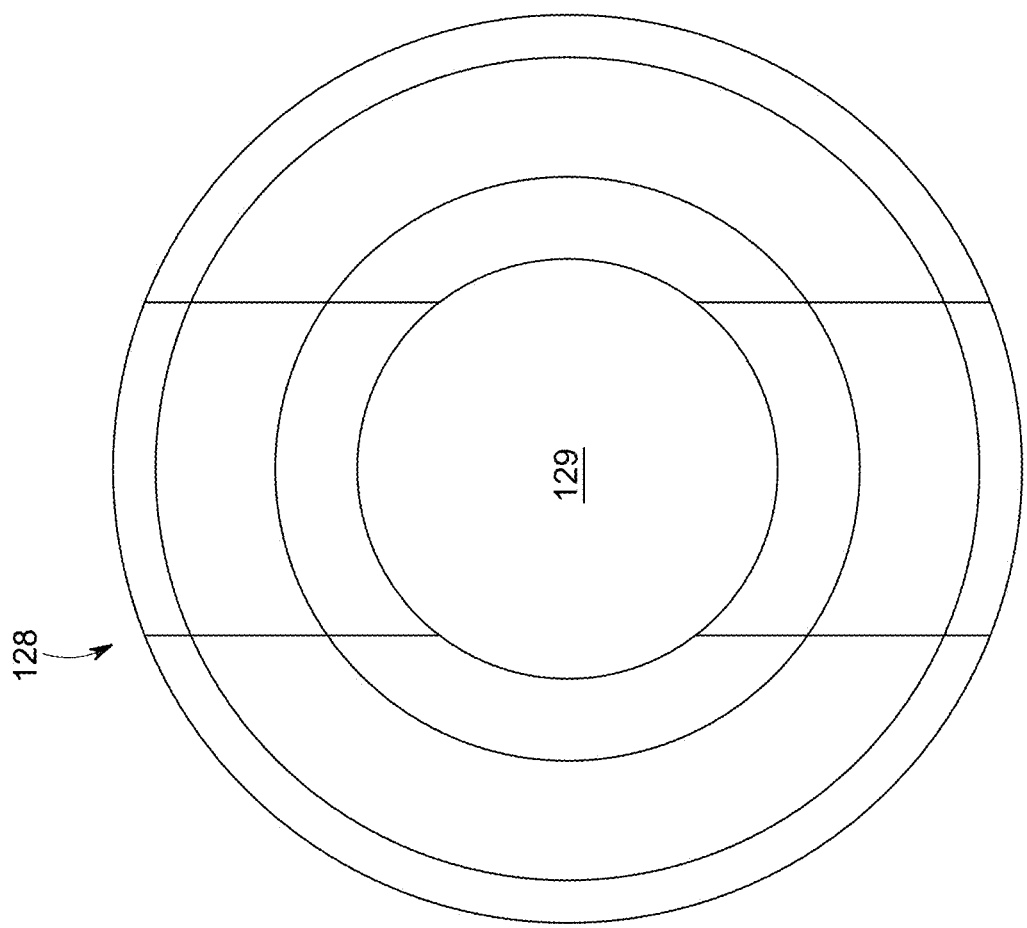
FIG. 32 illustrates an end view of the head post of FIG. 30, in accordance with an aspect of the present disclosure.
Figure 33:
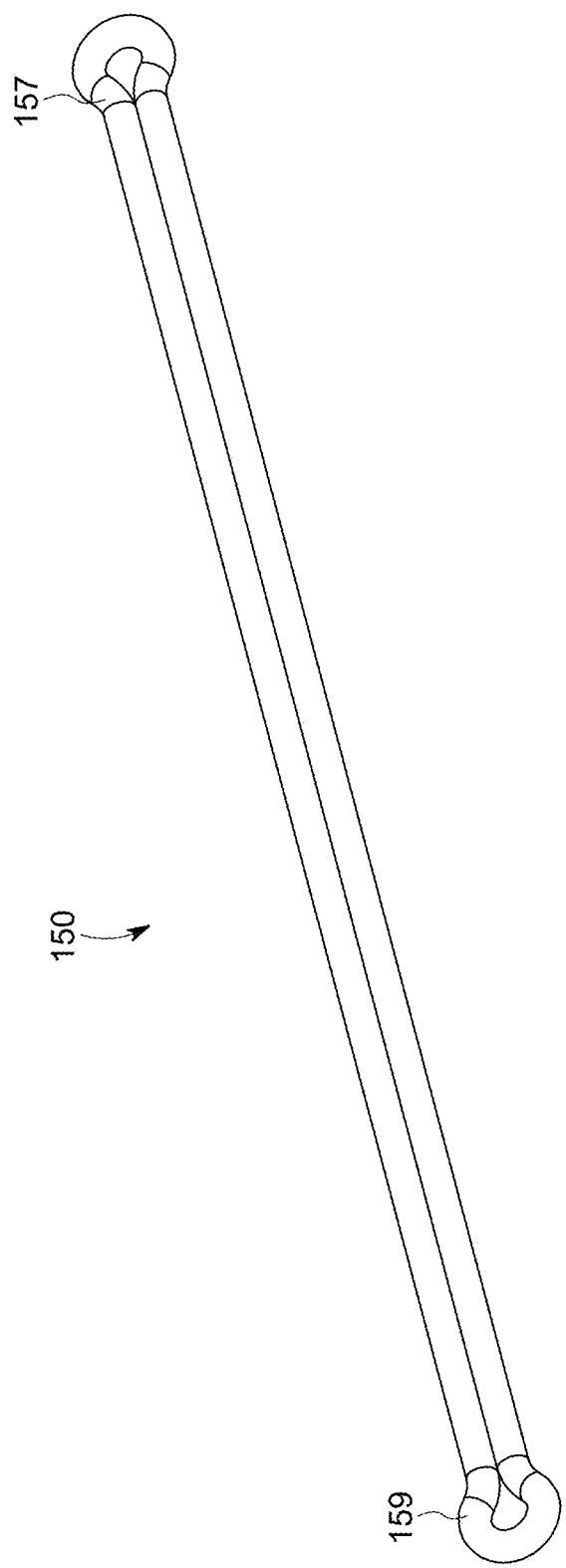
FIG. 33 illustrates a perspective view an exemplary tension member of the implant of FIG. 1, in accordance with an aspect of the present disclosure.
Figure 34:
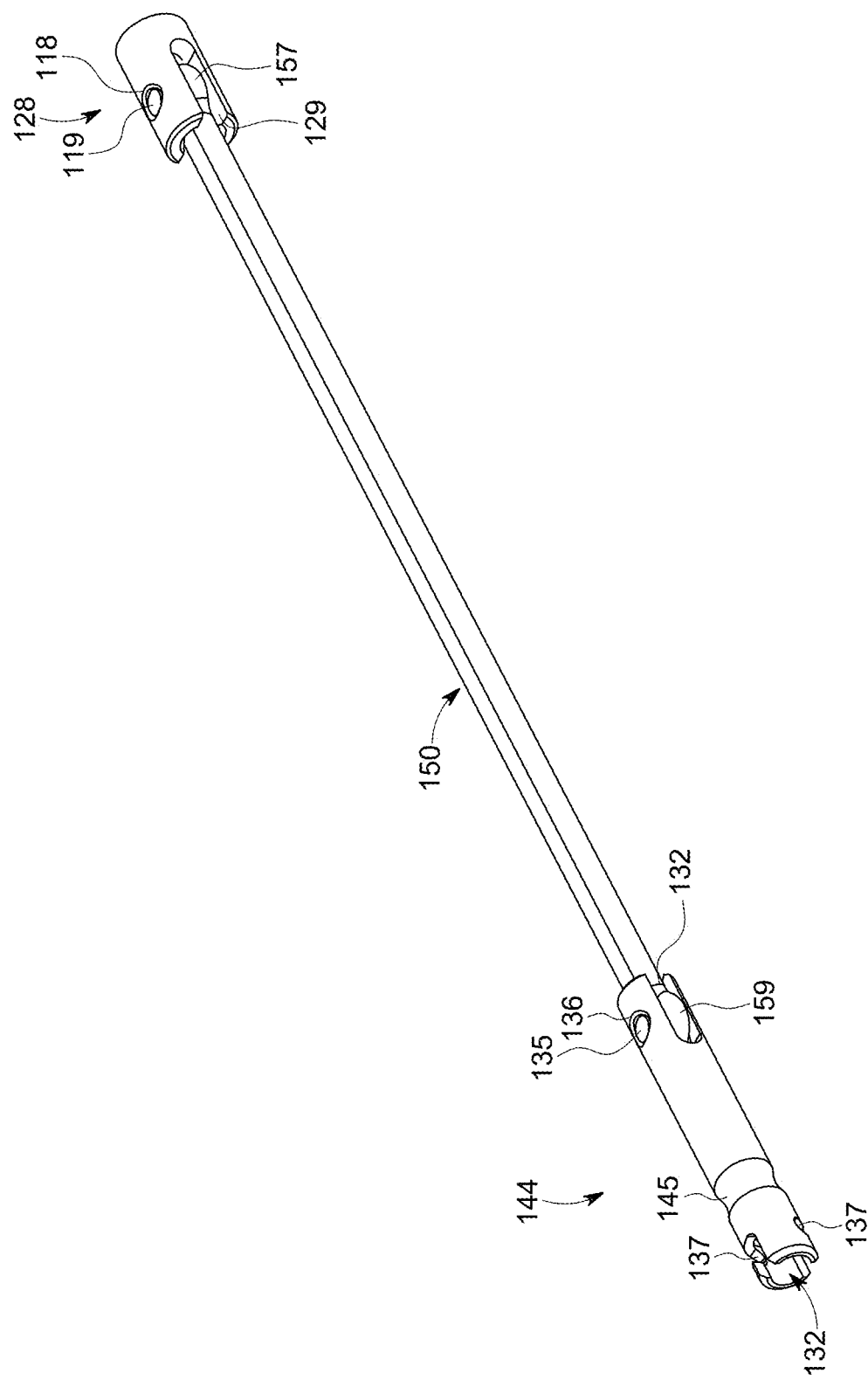
FIG. 34 illustrates a perspective view an assembly of the tension member of FIG. 33, the tip post of FIGS. 26-29 and the head post of FIGS. 30-32 of the implant of FIG. 1, in accordance with an aspect of the present disclosure.
Figure 35:
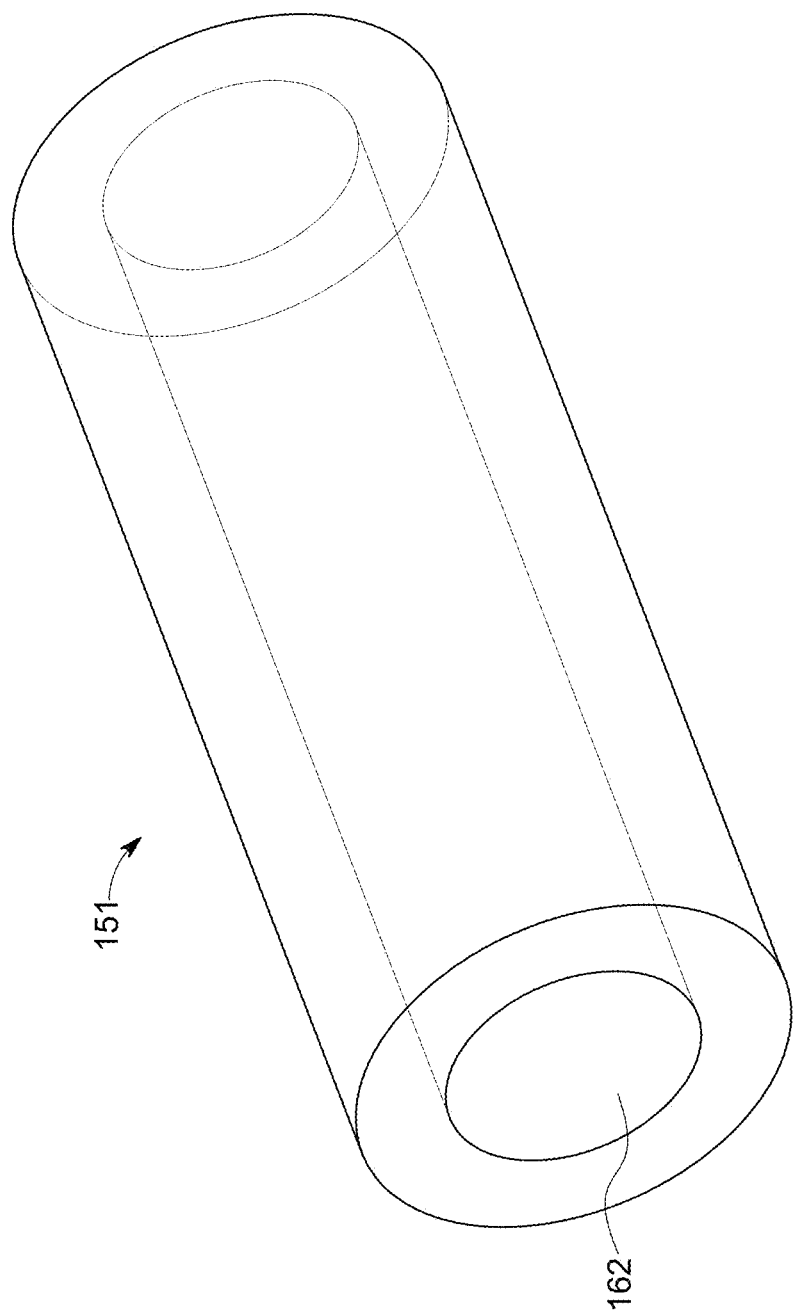
FIG. 35 illustrates a perspective view of an exemplary resilient member of the implant of FIG. 1, in accordance with an aspect of the present disclosure.

As shown in FIGS. 6, 7, 9, 10, 33 and 34, the constraint and/or tension member 150 may comprise a loop with first and second end portions 157, 159. As explained further below, the first and second openings ends 157, 159 of the opening or loop of the constraint and/or tension member 150 are configured to accommodate or accept pins extending through the loop and against the first and second end portions 157, 159, respectively, so that the constraint and/or tension member 150 can be pulled into tension (or apply tensile forces that act to pull the head portion 110 and the anchor portion 130 together). The first end portion 157 of the constraint and/or tension member 150 may be coupled to the head portion 110 within the cannulated opening 152 thereof via the head post 128, as shown in FIGS. 6, 7 and 25. The head post 128 may be contained or positioned within the enlarged portion 153 of the cannulated opening 152 of the head portion 110.

As shown in FIGS. 30-32 and 34, the head post 128 includes an axially/longitudinally extending through hole, cannulated opening or passageway 129 extending therethrough that is configured to allow the first end portion 157 of the constraint and/or tension member 150 loop to pass therethrough. The head post 128 also includes at least one laterally/radially extending pin aperture or hole 118 that extends from the exterior of the head post 128 to the exterior surface of the head post 128 (and thereby the cannulated opening 152). The first end portion 157 of the tension member 150 can be inserted or passed through the cannulated opening 129 of the head post 128 such that the opening of the loop of the tension member 150 is aligned with the pin aperture 918. With the opening of the tension member 150 being aligned with the pin aperture 118, a head pin 119 can be pressed into/through the pin aperture 118 and into/through the opening to fix the first end portion 157 of the constraint and/or tension member 150 to the head post 128, as shown in FIGS. 6,7, 30-32 and 34. In some embodiments, the head pin 119 may initially be partially disposed or pre-assembled within a portion of the pin aperture 118 prior to passing the constraint and/or tension member 150 through the cannulated opening 129.

Figure 8:
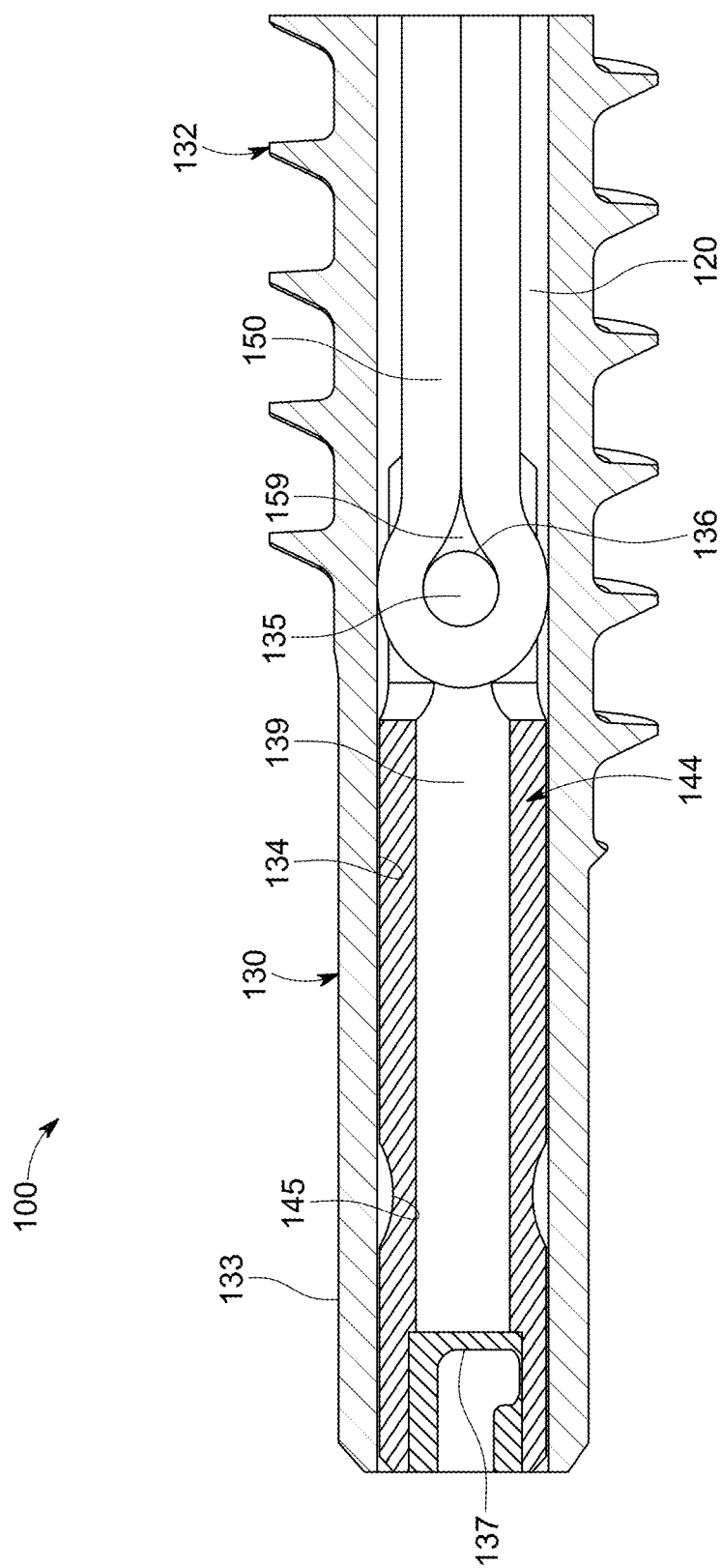
FIG. 8 illustrates a side cross-sectional view of another portion of the implant of FIG. 1, in accordance with an aspect of the present disclosure.
Figure 9:
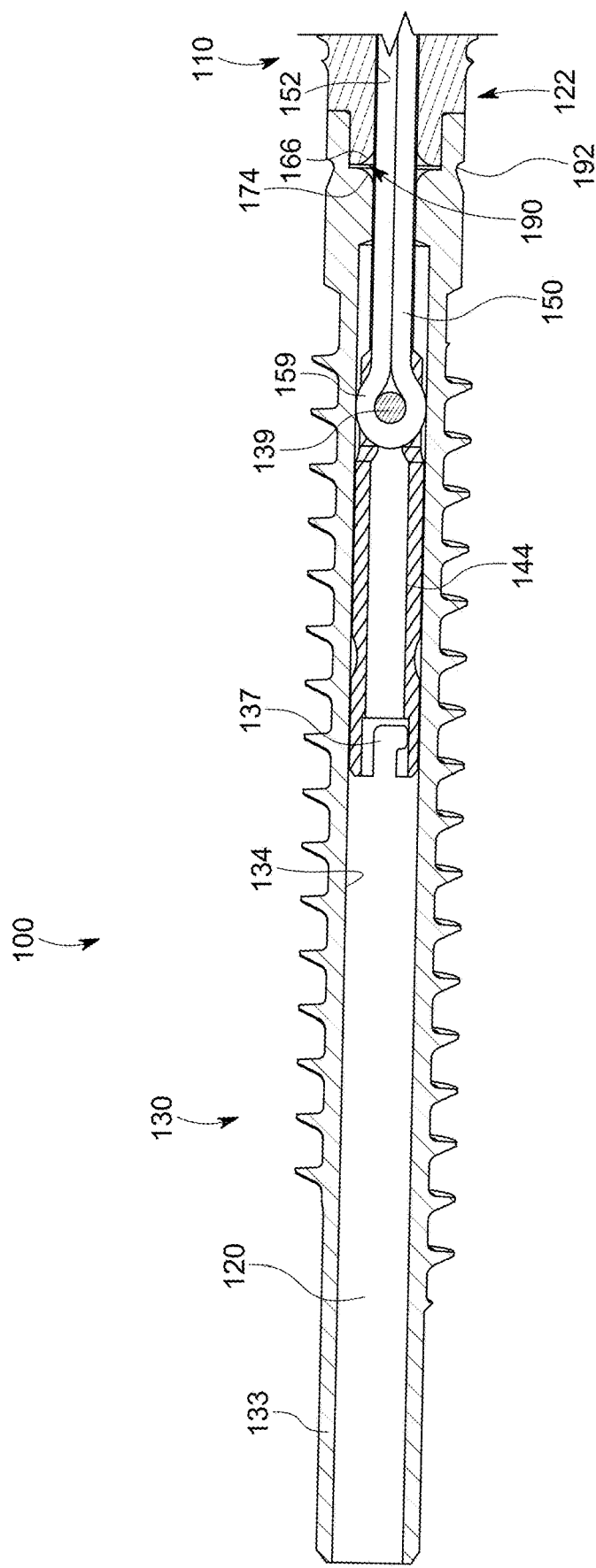
FIG. 9 illustrates a side cross-sectional view of another portion of the implant of FIG. 1, in accordance with an aspect of the present disclosure.

The second end portion 159 of the constraint and/or tension member 150 may be coupled to the anchor portion 130 within the cannulated opening 134 thereof via the tip post 144, as shown in FIGS. 6, 8, 9 and 34. The tip post 144 may be contained or positioned within the cannulated opening 134 of the anchor portion 130 (e.g., the cannulated opening 134 of the crimp portion 133 and/or the threaded shaft portion 132). Specifically, the cannulated opening 134 of the anchor portion 130 (e.g., the cannulated opening 134 of the crimp portion 133 and the threaded shaft portion 132) is configured to allow the tip post 144 to axially slide or translate therein in a neutral, natural or undeformed or un-crimped state, as shown in FIGS. 8 and 9. As explained further below, the crimp portion 133 of the anchor portion 130 may be inwardly deformed or crimped such that the cannulated opening 134 thereof is narrowed or partially collapsed to fixed or trap the tip post 144 within a particular or selected axial positioned or location within the cannulated opening 134 along the crimp portion 133 of the anchor portion 130 (not shown).

As shown in FIGS. 6, 8, 9 and 34, the tip post 144 includes an axially/longitudinally extending through hole, cannulated opening or passageway 139 extending therethrough that is configured to allow the second end portion 159 of the constraint and/or tension member 150 to pass therethrough. The tip post 144 also includes at least one laterally/radially extending pin aperture or hole 136 positioned proximate to a second end of the tip post 144. The pin aperture 136 extends from the exterior of the tip post 144 to the cannulated opening 139. The first end portion 157 of the tension member 910 can be inserted or passed through the cannulated opening 139 of the tip post 144 such that the opening thereof is aligned with the pin aperture 136. With the opening of the loop of the constraint and/or tension member 150 being aligned with the pin aperture 136, a tip pin 135 can be pressed into/through the pin aperture 136 and into/through the opening of the constraint and/or tension member 150 to fix the second end portion 159 of the constraint and/or tension member 150 to the tip post 144, as shown in FIGS. 6, 8, 9 and 34. In some embodiments, the tip pin 135 may initially be partially disposed or pre-assembled within a portion of the pin aperture 136 prior to passing the constraint and/or tension member 150 through the cannulated opening 139.

The tip post 144 also includes a hook slot 137 (e.g., a "J", "L" or "T" shaped slot) extending from a second end thereof, as shown in FIGS. 6, 8, 9, 26-29 and 34. The hook slot 137 may define a slot or passageway that is open to the second end of the tip post 144. The hook slot 137 is configured to allow a member (e.g., a suture, tool or other member or device) (not shown) to extend therein/therethrough to engage the tip post 144 and apply an axial tensioning force to the tip post 144, as shown by the difference in the axial position of the tip post 144 in FIGS. 8 and 9. When the tip post 144 is positioned within the cannulated opening 134 of the anchor portion 130, the member (not shown) may extend into the cannulated opening 134 and through/engage with the hook slot 137. A tensioning force may be applied to the tip post 144 via the hook slot 137 and the member therein/therethrough may act in a direction extending from the head portion 112 to the anchor portion 130 to translate the tip post 144 into the cannulated opening 134 of the crimp portion 133 of the anchor portion 130.

As shown in FIGS. 6, 8, 9, 26-29 and 34, the tip post 144 includes a crimp recess or groove 145 extending into the outer surface of the tip post 144. The crimp recess 145 may extend circumferentially about the tip post 144. The crimp recess 145 may be positioned between the hook slot 137 and the pin aperture 136. The crimp recess 145 is configured such that when the tip post 144 is positioned within the cannulated opening 134 of the anchor member 912, a space or gap is formed between the crimp recess 145 and the inner surface of the anchor member 912 forming the cannulated opening 134, as shown in FIGS. 8-10. In this way, as described above, the crimp portion 133 of the anchor portion 130 may be crimped (i.e., deformed inwardly) such that the side wall of the crimp portion 133 extends into the cannulated opening 134 and the crimp recess 145 (i.e., the cannulated opening 134 is narrowed or partially collapsed into the crimp recess 145) to fix or trap the tip post 144 within a particular or selected axial/longitudinal position or location within the cannulated opening 134 along the anchor portion 130.

As shown in FIGS. 1-18, 24 and 25, the exterior or outer surface of at least a portion of the crimp portion 133 of the anchor portion 130 may be of irregular or non-circular cross-section as a medial removal feature 198 for medial removal of the anchor portion 130 after breakage of the breakaway portion 160 of the implant 100 via rotation of the anchor portion 130. For example, as shown in FIGS. 1-18, 24 and 25, the exterior surface of at least a portion of the crimp portion 133 of the anchor portion 130 may define removal members positioned around the circumference of the anchor member 130 that can be engaged from a medial side and utilized to rotate the anchor portion 130 to remove the anchor portion 130 from a bone. In some embodiments, the removal members may comprise outer planar surfaces circumferentially arranged about the axis of the exterior surface of at least a portion of the crimp portion 133 of the anchor portion 130. For example, at least a portion of the exterior surface of the crimp portion 133 of the anchor portion 130 may comprise an external hexagonal portion, shape or drive feature 198, as shown in FIGS. 1-18, 24 and 25.

As shown in FIGS. 1-18, 24 and 25, the exterior or outer surface of at least a portion of the anchor portion 130 proximate to (but distal of) the breakaway coupling portion 138 may be of irregular or non-circular cross-section as a lateral removal feature 196 for lateral removal of the anchor portion 130 after breakage of the breakaway portion 160 of the implant 100 via rotation of the anchor portion 130. For example, as shown in FIGS. 1-18, 24 and 25, the lateral removal feature 196 (i.e., the exterior surface of at least a portion of the anchor portion 130 proximate to (but distal of) the breakaway coupling portion 138) may define removal members positioned around the circumference of the anchor member 130 that can be engaged from a lateral side and utilized to rotate the anchor portion 130 to remove the anchor portion 130 from a bone. In some embodiments, the removal members of the lateral removal feature 196 may comprise outer planar surfaces circumferentially arranged about the axis of the exterior surface of at least a portion of the anchor portion 130 proximate to (but distal of) the breakaway coupling portion 138. For example, at least a portion of the exterior surface of the anchor portion 130 proximate to (but distal of) the breakaway coupling portion 138 may comprise an external hexagonal portion, shape or drive feature 196 as shown in FIGS. 1-18, 24 and 25.

As shown in FIGS. 3, 6, 17 and 18, in some embodiments the anchor portion 130 (e.g., the breakaway coupling portion 138 thereof) may include a minor diameter that extends axially past the outer groove 102 that is greater than (or equal to) a minor diameter of the head portion 110. In some other embodiments, the anchor portion 130 (e.g., the breakaway coupling portion 138 thereof) may include a minor diameter that only extends axially to the outer groove 102 (i.e., not axially past) that is greater than (or equal to) a minor diameter of the head portion 110. The anchor portion 130 (e.g., the breakaway coupling portion 138 thereof) may thereby include a minor dimeter that is larger than that of the head portion 110 only to the outer groove 102. In this way, the outer groove 102 may be formed in a portion of the anchor portion 130 (e.g., in the breakaway coupling portion 138 thereof) that includes a minor diameter that is less than a minor diameter of the head portion 110.

In some embodiments, the coupling projection 164 of the breakaway coupling portion 122 of the head portion 110 may be fixedly coupled within the coupling cavity 172 of the breakaway coupling portion 138 of the anchor portion 130. For example, the coupling projection 164 of the breakaway coupling portion 122 of the head portion 110 and the coupling cavity 172 of the breakaway coupling portion 138 of the anchor portion 130 may be welded (e.g., laser welded) together. In some such embodiments, the weld may fully penetrate the breakaway coupling portion 122 of the head portion 110 and the breakaway coupling portion 138. For example, the interior surface of the coupling cavity 172 of the breakaway coupling portion 138 of the anchor portion 130 (e.g., a portion or entirety thereof) may be welded to (e.g., made integral with) the exterior surface the coupling projection 164 of the breakaway coupling portion 122 of the head portion 110 (e.g., to a portion or entirety thereof). Similarly, the proximal end surface of the coupling cavity 172 of the breakaway coupling portion 138 of the anchor portion 130 (e.g., a portion or entirety thereof) may be welded to (e.g., made integral with) the outer collar or stop surface 165 of the breakaway coupling portion 122 of the head portion 110 (e.g., to a portion or entirety thereof).

The breakaway coupling portion 122 of the head portion 110 and the breakaway coupling portion 138 of the anchor portion 130 may thereby be welded together at a weld zone that is positioned axially adjacent to the internal and external grooves 190, 192. Specifically, weld zone comprises a portion of the coupling projection 164 of the breakaway coupling portion 122 of the head portion 110 that is axially spaced (e.g., axially adjacent) from the internal end surface portion 166, and a portion of the coupling projection 164 of the breakaway coupling portion 122 of the head portion 110 that is axially spaced (e.g., axially adjacent) from the internal end surface portion 174. The breakaway portion 120 of the implant 100 and the weld zone may be configured such welded joint and the breakaway portion 120 (at the internal and external grooves 190, 192) withstand the torque necessary to implant the implant 100 into bones/bone segments (i.e., in targeted anatomy), and such that the implant 100 fails, break or fracture due to in situ forces (e.g., typical physiological forces experienced at the joint of the bones/bone segments, such as due to patient weightbearing) applied to the implant 100 at the location of the internal and external grooves 190, 192 and not at the weld zone/joint. In some other embodiments, the weld/weld zone may be configured such that the implant fails, break or fracture due to in situ forces applied to the implant 100 at the welded joint instead of at the internal and external grooves 190, 192.

The implant 100 may thereby be configured to fracture (due to in situ forces) at the location of the internal groove 190 formed via the internal end surface portion 166 of the head portion 110 and the internal end surface portion 174 of the anchor portion 130. The arcuate and/or beveled configuration/nature of the internal end surface portion 166 of the head portion 110 and the internal end surface portion 174 of the anchor portion 130 provide relatively smooth, dull and/or protective internal end surfaces of the fractured/separated head portion 110 and anchor portion 130 to prevent the constraint and/or tension member 150 from becoming abraded, cut, worn, frayed or otherwise deteriorated by the end surface surfaces of the fractured/separated head portion 110 and anchor portion 130. In this way, internal groove 190 formed via the arcuate and/or beveled internal end surface portion 166 and internal end surface portion 174 prevent the formation of a sharp and/or jagged internal edge of the implant 100 that would contact the constraint and/or tension member 150 and thereby abrade, cut, wear, fray or otherwise deteriorate the constraint and/or tension member 150.

The internal circumferential groove 190 and the external circumferential groove 192 of the breakaway portion 160 may cooperate to form a portion of the implant 100 with the thinnest wall portion or radial thickness from the cannulated opening 120 to the exterior surface thereof. The internal circumferential groove 190 and the external circumferential groove 192 of the breakaway portion 160 may be configured to concentrate stress thereat such that the implant 100 fractures/separates at the breakaway portion 160 (at the location of the circumferential groove 190 and the external circumferential groove 192, such as between the circumferential groove 190 and the external circumferential groove 192) via forces acting on the implant 100 to separate the head portion 110 and the anchor portions 130. It is noted that a proximal end portion of the breakaway coupling portion 138 may remain coupled (e.g., welded) to the head portion 110 when the breakaway portion 160 fractures/separates).

The implant 100 may have, for example, a breakaway feature ratio between the wall or radial thickness of the implant 100 at the internal and external grooves 190, 192 as compared to that of an adjacent or proximate portion of the head portion 110 and/or the anchor portion 130 within the range of 64% to 89%, or within the range of 75% to 82%. As noted above, the implant 100 may be configured such that the stress applied to the implant 100 in situ is concentrated at/to the breakaway portion 120 (e.g., the circumferential internal and external grooves 190, 192 thereof). In some embodiments, the breakaway portion 120 may be configured to fail (i.e., fracture) due to an initial application of a typical physiological forces experienced at the joint of the bones/bone segments, such as due to an initial patient weightbearing. In some embodiments, the breakaway portion 120 may be configured to fail (i.e., fracture) in fatigue due to such stresses.

The implant 100 may thereby provide a first period of substantially rigid fixation of the bones/bone segments, and then after the failure of the breakaway portion 120, a second phase of semi-constrained and/or dynamic motion between the bones/bone segments (provided by the constraint and/or tension member 150). For example, the implant 100 may be inserted into a tibia and fibula after a syndesmotic reduction to temporarily fix the tibia and fibula, but to allow semi-constrained and/or dynamic motion thereafter. In some such embodiments, the implant 100 may be inserted into a tibia and fibula following a repair of an ankle fracture, such as a fibula fracture.

The implant 100 may thereby initially fully support the bones/bone segment, such as for a sufficient time period for one or more syndesmotic ligament to heal post-operatively. The implant may also, for example, selectively constrain motion in all directions to allow one or more the ligaments to heal. For example, as the period of full or rigid support that allows for one or more syndesmotic ligament to heal, the implant 100 allows for physiologic motion.

The implant 100 also allow for screw-like implantation and temporary rigid fixation, then, after insertion, the implant 100 are designed to break away (e.g., fracture and/or dissolve) at the breakaway portion 120 after one or more loading cycle (e.g., a number of loading cycles that may differ according to load). The at least one loading cycle may be a plurality of non-weight bearing and/or weight bearing loading cycles, or a single non-weight bearing and/or weight bearing loading cycle. In some embodiments, the implant 100 may be designed to fail (i.e., fracture or break) in fatigue at the breakaway portion. In some embodiments, the implant 100 may be designed to concentrate forces that are applied to the implant 100 (e.g., after implantation/in situ) at/to the breakaway portion 120 such that failure (e.g., fatigue fracture) occurs at the at the breakaway portion 120, as explained above. The temporary rigid fixation of the implant 100 gives the fixed joint time to stabilize through healing and then allows physiologic motion after breakaway (e.g., fracture) of the breakaway portion 120. The breakaway location can be set in a space or gap between the bones/bone segment (e.g., between a fibula and tibia), where the subsequent risk of damage to native bone is lower. In this way, forces and/or stress applied to the implant 100 after implantation may be concentrated to the breakaway portion 120, which may be configured to fail (e.g., fracture) due to the loading. In some embodiments, the configuration of the internal and external grooves 190, 192 may be optimized to provide or survive sufficient torque such that the implant 100 can be implanted via rotation thereof, and provide a bending performance that fails when loads are applied to the implant in situ (e.g., loads angled with respect to the axis of the implant and/or between the bones/bone segments).

The head portion 110 and/or anchor portion 130 may remain in a bone/bone segments after failure of the breakaway portion 120 (e.g., in a patient's fibula and tibia, respectively). However, if hardware removal is required/desired, the head portion 110 may be removed from the respective bone/bone segment after the breakaway portion 102 fractures, such as via the tool engagement opening 114. In addition, if necessary/desired, the anchor portion 130 may be removed from the respective bone/bone segment. The anchor portion 130 may be removed from the respective bone/bone segment, for example, medially using the distal drive feature 198 or laterally using the lateral removal member 196.

The implant 100 may be assembled (i.e., the anchor portion 130 and the head portion 110 dynamically linked by the constraint and/or tension member 150, the at least one resilient member 151 and the breakaway portion 120) by seating/positioning the coupling projection 164 of the breakaway coupling portion 122 of the head portion 110 within the coupling cavity 172 of the breakaway coupling portion 138 of the anchor portion 130, as described above. As also described above, the breakaway coupling portion 122 of the head portion 110 and the breakaway coupling portion 138 of the anchor portion 130 may be welded (e.g., laser welded) together.

Assembling the impact 100 may also comprise positioning the second end portion 159 of the constraint and/or tension member 150 within the cannulated opening 139 of the tip post 144, and inserting and the tip pin 135 through the pin aperture 136 of the tip post 144 such that the tip pin 135 extends through the second end opening 159 to couple the constraint and/or tension member 150 and the tip post 144 (i.e., to capture the constraint and/or tension member 150 in the tip post 144), as shown in FIG. 8.

The pre-assembled constraint and/or tension member 150 and tip post 144 may be assembled with the anchor portion 130, the head portion 110, the at least one resilient member 151 and the head post 128. For example, the first end portion 157 of the constraint and/or tension member 150 may be inserted into and through the cannulated opening 134 of the anchor portion 130 via the opening at the end of the crimp portion 133, into and through the cannulated opening 152 of the head portion 110, into and through the through hole 162 of the at least one resilient member 151 (if the through hole is provided), and into and through the cannulated opening 152 of the head post 128. The constraint and/or tension member 150 may be positioned within the cannulated openings of the implant 100 such that the tip post 144 is also positioned or translated into the cannulated opening 134 of the anchor portion 130.

With the first end portion 157 of the constraint and/or tension member 150 positioned within the cannulated opening 152 of the head post 128, the head pin 119 may be pressed or otherwise translated through the pin aperture 118 of the head post 128 such that the head pin 119 extends through the opening of the first end portion 157 to couple the constraint and/or tension member 150 and the head post 128 (i.e., to capture the constraint and/or tension member 150 in the head post 128), as shown in FIG. 7. The at least one resilient member 151 may also thereby be seated within the enlarged portion 153 of the cannulated opening 152 of the head portion 112.

With the constraint and/or tension member 150 and the head post 128 coupled, the constraint and/or tension member 150 may be tensioned via the hook slot 137 of the tip post 144 to axially seat, engage or assemble the components of the implant 100 and apply the assembly tension. For example, a member or tool (e.g., a suture) (not shown) may be inserted into the cannulated opening 134 of the anchor portion 130 and engaged with the hook slot 137 of the tip post 144. The tip post 144 and constraint and/or tension member 150 may initially be positioned distal to the free end or tip of the anchor portion 130 (formed by the crimp portion 133) within the cannulated opening 134. The member or tool may be tensioned to "pull" the tip post 144 via the hook slot 137 axially/longitudinally through the cannulated opening 134 of the anchor portion 130 proximate to the free end or tip of the anchor portion 130 within the cannulated opening 134. The constraint and/or tension member 150 may thereby also be axially/longitudinally translated through the cannulated opening 152 of the head portion 112, which causes the head post 128 to seat within the enlarged portion 153 of the cannulated opening 152 of the head portion 110 and act against the at least one elastic member 151 to trap the at least one elastic member 151 between the narrow portion 155 of the cannulated opening 152 and the head post 128, as shown in FIG. 8. Axial/longitudinal translation of the constraint and/or tension member 150 through the cannulated opening 134 of the anchor portion 130 may also cause head portion 110 to act against the at least one elastic member 151 and fully seat the coupling projection 164 of the breakaway coupling portion 122 of the head portion 110 within the coupling cavity 172 of the breakaway coupling portion 138 of the anchor portion 130, if not already fully seated therein.

Further axial/longitudinal transition of the tip post 144 and the second end 159 of the constraint and/or tension member 150 through the cannulated opening 134 of the anchor portion 130 toward the free end or tip of the anchor portion 130 (via "pulling" or tensioning via the hook slot 137) causes the head post 128 to compress the at least one resilient member 151 (between the head post 128 and the end of the enlarged portion 153 of the cannulated opening 152 of the head portion 110) to elastically deform the at least one resilient member 151. The at least one resilient member 151 may thereby apply the assembly tension force to the anchor portion 130 and the head portion 110 via the constraint and/or tension member 150 acting to pull (or push) the anchor portion 130 and the head portion 110 together. The at least one resilient member 151 may only be partially elastically compressed or deformed so that in situ forces can be dissipated or absorbed by further deformation thereof. To fix or maintain the assembly force, the position of the tip post 144 proximate to the free end or tip of the anchor portion 130 within the cannulated opening 134 may be fixed or maintained via crimping or inwardly deforming the crimp portion 133 of the anchor portion 130 into the crimp recess 145 of the tip post 144 (not shown).

Referring now to FIGS. 36-39, there is illustrated an alternate embodiment of an implant 200. In some aspects, the implant 200 may contain one or more components or features of the implant 100 as shown and described previously. The implant 200 may also contain additional and/or alternate features to those shown and described with reference to the implant 100. Similar to the implant 100, the implant 200 may be configured to heal syndesmotic ligaments post-operatively, where said implant 200 is configured to selectively constrain motion between two or more bones in all directions to allow for one or more ligaments extending there between to heal. Furthermore, after the one or more ligaments have healed, the implant 200 may be configured to allow physiologic motion between the bones or bone segments. With reference to syndesmotic ligaments, the implant 200 may also be configured to create, re-create, and/or relieve pressure in the lateral gutter of the ankle.

Figure 36:
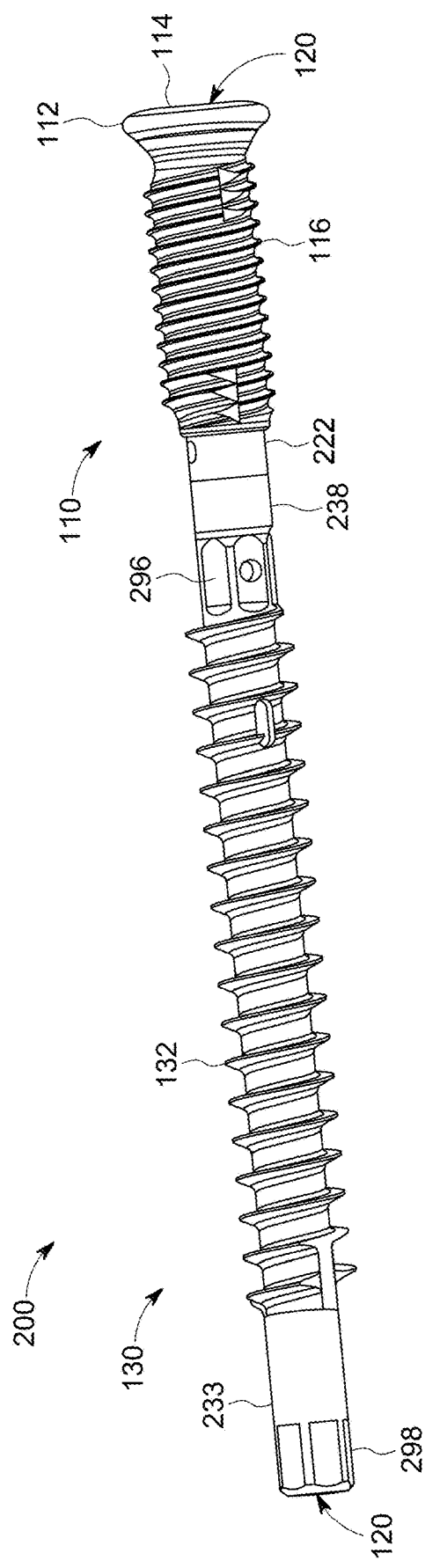
FIG. 36 illustrates a side view of an alternate embodiment of an exemplary dynamic fixation implant, in accordance with an aspect of the present disclosure.

The implant 200 is shown in FIG. 36 to include the head portion 110 and the anchor portion 130 as shown previously with reference to the implant 100. The head portion 110 and the anchor portion 130 may include all components as shown and described previously with reference to the system 100 and may also have one or more of the components subsequently shown and described in place of the components of the implant 100. The head portion 110 is shown to include a breakaway coupling portion 222 located at a proximal first end of the head portion 110. The breakaway coupling portion 222 is shown to have an increased length (e.g., relative to the breakaway coupling portion 122) along a longitudinal axis of the implant 100 (e.g., an axis running through the implant such as circumferentially centered within the cannulated opening 120).

Figure 37:
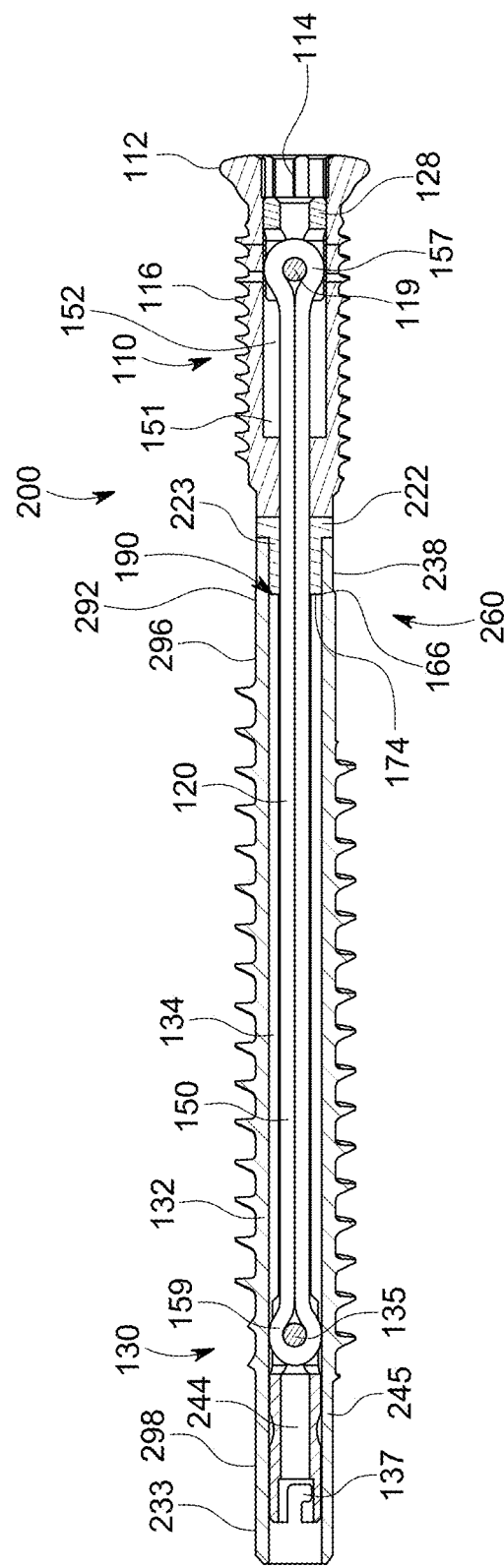
FIG. 37 illustrates a side cross-sectional view of the implant of FIG. 36, in accordance with an aspect of the present disclosure.

As shown in at least FIG. 37, the breakaway coupling portion 222 is shown to extend into the anchor portion 130 of the implant 200. In some aspects, the breakaway coupling portion 222 may extend further into the anchor portion 130 than the breakaway coupling portion 122 of implant 100. Further, the breakaway coupling portion 222 may have a lesser diameter than that of the breakaway coupling portion 122 so as to facilitate implantation and/or removal (e.g., removal after the implant 200 has fractured in a manner that is the same as or similar to that shown and described previously with reference to the implant 100). Additionally, the lesser diameter of the breakaway coupling portion 222 may facilitate removal of the head portion 110 in the instance wherein the head portion 110 and/or the implant 200 is removed from a patient (e.g., in the instance of infection).

Figure 38:
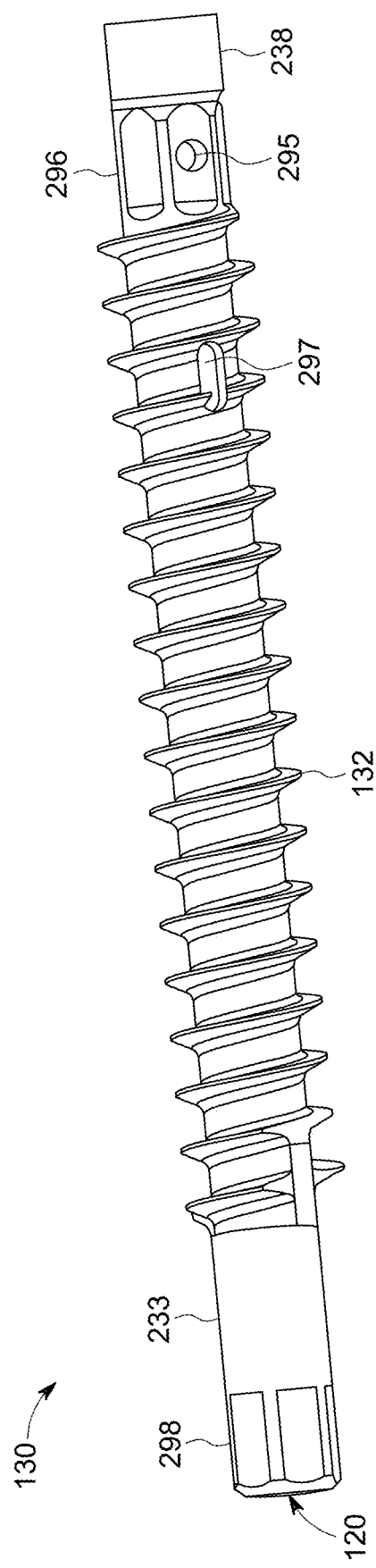
FIG. 38 illustrates a perspective view of a portion of the implant of FIG. 36, in accordance with an aspect of the present disclosure.

The anchor portion 130 of the implant 200 is shown to include a breakaway coupling portion 238 as a proximal first end portion of the anchor portion 130 which, collectively with the breakaway coupling portion 222, forms a breakaway portion 260 (see FIG. 37). As shown in FIGS. 36-38, the breakaway coupling portion 238 has a length along a longitudinal axis of the implant 200 (e.g., an axis running through the implant such as circumferentially centered within the cannulated opening 120) greater than the breakaway coupling portion 138 of the implant 100. The aforementioned length of the breakaway coupling portion 238 may have a lateral dimension (e.g., cross-sectional) greater than at least a portion (e.g., a protrusion 223 as shown in FIG. 37) of the breakaway coupling portion 222 so as to accommodate at least a portion of the breakaway coupling portion 222 within at least a portion of the breakaway coupling portion 238 and facilitate complementary movement of these components. The breakaway coupling portion 238 includes the internal end surface portion 174 which may have the same and/or similar geometry as shown and described with reference to the implant 100. Similarly, the internal end surface portion 166 may be arranged adjacent to and/or abut the internal end surface portion 174 when the implant 200 is assembled. In some aspects, the internal end surface portion 166 and the internal end surface portion 174 may be positioned such that at least the outer diameters of at least a portion of the breakaway coupling portion 222 and the breakaway coupling portion 238 abut one another.

The anchor portion 130 of the implant 200 is further shown to include an external circumferential groove 292 disposed on an external surface of the breakaway coupling portion 238. In some aspects, the external circumferential groove 292 may have a geometry and/or dimensions that is the same as and/or similar to those of the external circumferential groove 192. The external circumferential groove 292 has a surface (extending circumferentially around the breakaway coupling portion 238) and accordingly, a corresponding geometry based on the size and/or dimensions (e.g., diameter, etc.) of the breakaway coupling portion 238. For example, in some aspects, the breakaway coupling portion 238 (and, accordingly, the breakaway coupling portion 222) may have a greater or lesser diameter across one or more portions thereof relative to the breakaway coupling portion 138 (or in the case of the breakaway coupling portion 222, relative to the breakaway coupling portion 122). Similar to the external circumferential groove 192, the external circumferential groove 292 may include a notch, groove, necking, or recess into the exterior surface of the breakaway coupling portion 238 and may further have curved/arcuate/rounded and/or flat/planar sides. Additionally, the external circumferential groove 292 may be arranged relative to the internal groove 190 as described with reference to the external circumferential groove 192 as shown and described previously above.

Figure 39:
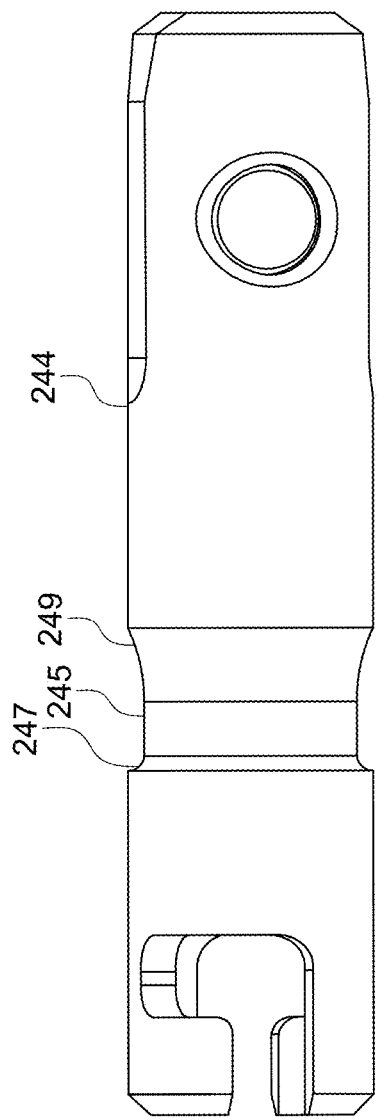
FIG. 39 illustrates an enlarged side view of a portion of the implant of FIG. 36, in accordance with an aspect of the present disclosure.

The implant 200 is also shown to include a tip post 244 as shown in FIGS. 37 and 39. The tip post 244 may be configured to have one or more geometries and/or dimensions the same as or similar to those of the tip post 144 as shown and described with reference to the implant 100. For example, the tip post 244 may be configured to interface with the tension member 150 within the anchor portion 130 in a manner that is the same as and/or similar to that of the tip post 144. The tip post 244 is shown to include a crimp recess 245 arranged on an outer surface of the tip post 244 and extending circumferentially around a portion of the exterior surface of the tip post 244. In some aspects, the crimp recess 245 may be arranged on the tip post 244 in a position that is the same as and/or similar to that of the tip post 144. In some aspects, at least a portion of the crimp recess 245 may be positioned at a lesser angle relative to the horizontal than the crimp recess 145. The crimp recess 245 is shown to include a distal portion 247 and a proximal portion 249, both of which extend circumferentially around at least a portion of the outer surface of the tip post 244 are disposed within the crimp recess 245. At least a portion of the distal portion 247 includes a vertical segment (e.g., substantially perpendicular to the longitudinal axis of the implant 200 and/or the tip post 244), with said vertical segment configured to increase retention (e.g., against a force applied substantially along the longitudinal axis of the implant 200) of the crimp portion 233 after crimping (e.g., once at least a portion of the crimp portion 233 has been crimped and is positioned within at least a portion of the crimp recess 245). The distal portion 247 is further shown to include at least a partial radius which, as shown in FIG. 39, is disposed radially inward from the vertical segment (e.g., closer to a longitudinal axis running through the tip post 244). The proximal portion 249 of the crimp recess 245 is shown to include a partial radius which may have the same and/or similar dimensions to the partial radius of the distal portion 247. Further, the dimensions (e.g., depth, length, etc.) of the crimp recess 245 may be similar to that of the crimp recess 145 as shown and described with reference to the implant 100.

The anchor portion 130 is further shown in FIGS. 36-38 to include a lateral removal feature 296 arranged about the exterior surface of the breakaway coupling portion 238. In some aspects, the lateral removal feature 296 may have a geometry similar to that of the lateral removal feature 196 of the implant 100. The lateral removal feature 296 may be configured to have an irregular or non-circular cross-sectional geometry (e.g., hex shaped, convexities and/or concavities, etc.) so as to accommodate one or more instruments to facilitate lateral removal of the anchor portion 130. As shown in FIGS. 36-38, the lateral removal feature 296 is arranged directly proximal to the external circumferential groove 292 and directly distal to the threads of the threaded shaft portion 132. The lateral removal feature 296 may have a length along the longitudinal axis of the implant 200 that is lesser than the length of the lateral removal feature 196 along the longitudinal length of the implant 100. Accordingly, the decreased length of the lateral removal feature 296 may complement an increased longitudinal length of the external circumferential groove 292. Additionally, the lateral removal feature 296 may include an aperture 295 (e.g., a recess, a bore, a detent, etc.) extending radially/diametrically from the surface of the lateral removal feature 296 into and/or through the breakaway coupling portion 238. The aperture 295 may be configured to accommodate one or more instruments and/or methods for implanting and/or removing the anchor portion 130 from a patient. The anchor portion 130 is further shown to include an aperture 297 (e.g., a recess, a bore, a detent, etc.) extending radially/diametrically from the surface of the threaded shaft portion 132 into and/or through the threaded shaft portion 132. The aperture 297 may be configured to accommodate one or more instruments and/or methods for implanting and/or removing the anchor portion 130 from a patient. In some aspects, the apertures 295, 297 may be configured to facilitate sterilization and/or other similar procedures. For example, the apertures 295, 297 may be configured so as to receive ethylene oxide gas or other sanitizing gases so as to facilitate sanitization of the internal components of the implant 200. In some aspects, the implant 200 may include three or more apertures that are the same as and/or similar to the apertures 295, 297 with the apertures arranged variously about the implant 200 and the components thereof.

The anchor portion 132 is further shown to include a crimp portion 233 at a distal end of the anchor portion 130 (e.g., arranged opposite the anchor portion 130 from the breakaway coupling portion 238). The crimp portion 233 is configured to have a medial removal feature 298 configured to facilitate medial removal of the anchor portion 130 of the implant 200 (for example, after breakage of the breakaway portion 260 of the implant 200). The crimp portion 233 is shown to have a flat surface arranged directly adjacent to the threaded shaft portion 132, with the medial removal feature 298 arranged opposite the flat surface relative to the threaded shaft portion. In some aspects, the medial removal feature 298 may have a geometry similar to that of the medial removal feature 198 of the implant 100. The medial removal feature 298 may be configured to have an irregular or non-circular cross-sectional geometry (e.g., hex shaped, convexities and/or concavities, etc.) so as to accommodate one or more instruments to facilitate medial removal of the anchor portion 130.

With reference to the implants 100, 200 and the components thereof, all of which may be composed of one or more of the same and/or similar materials identified previously. The implant 200 may also be configured to have dimensions (e.g., length, cross-sectional width, circumference, diameter, etc.) that are the same as or similar to the implant 100. Additionally, the implant 200 may be implemented in a surgical procedure in the same or similar manner to the implant 100 which may include, for example, following the same/similar steps for a surgical procedure and/or using the same/similar instrumentation.

The assembled implants 100, 200 may then be implanted into first and second bones/bone segments. For example, the assembled implant 100 may be implanted or inserted into first and second bones with the breakaway portion 120 at least partially positioned in a joint or space therebetween. As described above, the breakaway portion 120 will eventually fail leaving the head portion 110 coupled to the anchor portion 130 by only the constraint and/or tension member 150. The breakaway portion 120 may fail, for example, after the bones/implant 100 is physiologically loaded. Failure of the breakaway portion 120 will allow for semi-constrained motion between the first and second bones via the constraint and/or tension member 150 and the at least one resilient member 151. The flexibility of the at least one resilient member 151 (and potentially the constraint and/or tension member 150) may allow for diastatic motion of the implant 100. Thus, the implant 100 may allow for restoration of a patient's physiologic motion, as well as allowing for diastatic motion and/or pressure spikes, for example.

As may be recognized by those of ordinary skill in the art based on the teachings herein, numerous changes and modifications may be made to the above-described and other embodiments of the present disclosure without departing from the scope of the disclosure. The head member, anchor member, tension member, coupling, and other components of the implant and/or system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants and systems may include more or fewer components or features than the embodiments as described and illustrated herein. Accordingly, this detailed description of the currently-preferred embodiments is to be taken in an illustrative, as opposed to limiting of the disclosure.

Similarly, positions or directions may be used herein with reference to anatomical structures or surfaces. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation and methods, and the aspects, components, features and the like thereof, described herein with respect to the right leg may be mirrored so that they likewise function with the left leg. Further, the implants, devices, instrumentation and methods, and the aspects, components, features and the like thereof, disclosed herein are described with respect to the leg for brevity purposes, but it should be understood that the implants, devices, instrumentation and methods may be used with other bones of the body having similar structures.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. An implant, comprising:
    a head portion at a proximal end of the implant, comprising external threads and a first axial through hole;
    an anchor portion extending from the head portion at a distal end of the implant comprising external threads and a second axial through hole in communication with the first axial through hole; and
    a flexible constraint member extending within the first and second axial through holes comprising a first end portion coupled to the head portion and a second end portion coupled to the anchor portion,
    wherein at least one of the head portion and the anchor portions forms a breakaway portion configured to concentrate stress thereat such that the implant fractures at the breakaway portion via forces acting on the implant to separate the head and anchor portions, and
    wherein the breakaway portion comprises an external circumferential groove and an internal circumferential groove axially aligned with the external groove, the internal circumferential groove formed between a radially-extending internal end surface portion of the head portion and a radially-extending internal end surface portion of the anchor portion, and
    wherein the head portion and the anchor portion are separate and distinct components that are welded together at a weld zone that is axially adjacent to the external and internal circumferential grooves such that the weld zone is axially spaced from the radially-extending internal end surface portion of the head portion and the radially-extending internal end surface portion of the anchor portion.

2. The implant according to claim 1, wherein the internal end surface portion of the head portion comprises a radially-extending internal arcuate end surface portion of the head portion, and the internal end surface portion of the anchor portion comprises a radially-extending internal arcuate end surface portion of the anchor portion.

3. The implant according to claim 1, wherein the internal end surface portion of the head portion comprises a radially-extending internal beveled end surface portion of the head portion, and the internal end surface portion of the anchor portion comprises a radially-extending internal beveled end surface portion of the anchor portion.

4. The implant according to claim 1, wherein a proximal end portion of the anchor portion comprises a coupling cavity and a distal end portion of the head portion comprises a coupling projection corresponding to the coupling cavity, the coupling projection being received within the coupling cavity.

5. The implant according to claim 4, wherein a bottom portion of the coupling cavity defines the internal end surface portion of the anchor portion, and a tip portion of the coupling projection defines the internal end surface portion of the head portion.

6. The implant according to claim 1, wherein the flexible constraint member comprises an elastic suture loop.

7. The implant according to claim 1, further comprising an anchor post member positioned within the second axial through hole and coupled with the flexible constraint member, wherein the anchor post member comprises an external groove, and wherein a proximal coupling portion of the anchor member is deformed into the external groove.

8. The implant according to claim 1, wherein the head portion comprises:
    a shaft portion with a first end and a second end;
    a head extending from the first end of the shaft portion; and
    a first breakaway coupling portion extending from the second end of the shaft portion.

9. The implant according to claim 8, wherein a portion of the shaft portion of the head portion comprises external threads.

10. The implant according to claim 8, wherein the head comprises a non-circular drive opening at an axial free end thereof, the non-circular drive opening forming a portion of the first axial through hole.

11. The implant according to claim 8, wherein the first breakaway coupling portion comprises a coupling projection with an inner surface that defines the internal end surface portion of the head portion, the inner surface of the coupling projection forming a portion of the first axial through hole.

12. The implant according to claim 11, wherein the first breakaway coupling portion further comprises a stop surface extending radially from an outer surface of the coupling projection and positioned axially between the internal end surface portion thereof and the head.

13. The implant according to claim 12, wherein the anchor portion comprises a second breakaway coupling at a first end thereof comprising a coupling cavity with an inner bottom surface that defines the internal end surface portion of the anchor portion, the inner surface of the coupling projection forming a portion of the first axial through hole.

14. The implant according to claim 13, wherein the coupling projection is mated within the coupling cavity.

15. The implant according to claim 14, wherein the coupling projection and the coupling cavity comprise the weld zone such that they are welded together.

16. The implant according to claim 13, wherein an end surface of the second breakaway coupling abuts the stop surface of the first breakaway coupling.

17. The implant according to claim 12, wherein the anchor portion further comprises:
a shaft portion with a first end and a second end; and
a crimp portion extending from the second end, and
wherein the second breakaway coupling extends from the first end of the shaft portion.

18. The implant according to claim 17, wherein a portion of the shaft portion of the anchor portion comprises external threads.

19. The implant according to claim 17, wherein a proximal portion of the shaft portion of the anchor portion comprises a plurality of outer circumferentially arranged planar surfaces forming a proximal external drive feature.

20. The implant according to claim 1, wherein the first axial through hole of the head portion comprises a first enlarged portion positioned proximate to a proximal end of the head portion and a second narrow portion positioned proximate to the breakaway portion, and further comprising a head post member positioned within the first enlarged portion of the first axial through hole and coupled to the first end portion of the flexible constraint member.

21. The implant according to claim 20, further comprising at least one resilient member positioned within the first enlarged portion of the first axial through hole axially between the second narrow portion thereof and the head post member.

22. The implant according to claim 21, wherein the second narrow portion, the at least one resilient member and the head post member are configured such that the at least one resilient member and the head post member are prevented from axially translating through the second narrow portion.

23. The implant according to claim 21, wherein the at least one resilient member comprises at least one tube formed of thermoplastic urethane, polycarbonate urethane or a combination thereof.

24. The implant according to claim 1, wherein the flexible constraint member comprises a suture loop.

25. The implant according to claim 1, comprising a cannulated opening extending through an entire axial length of the implant.

26. The implant according to claim 1, wherein a radial thickness of the breakaway portion extending between the internal and external circumferential grooves is a thinnest wall portion of the implant.

27. The implant according to claim 1, wherein the breakaway portion comprises a medial portion of the implant that is void of external threads.

28. The implant according to claim 1, wherein the internal circumferential groove comprises a space between the radially-extending internal end surface portion of the head portion and the radially-extending internal end surface portion of the anchor portion.

* * * * *